United States Patent [19]

Yokoyama et al.

[11] Patent Number: 5,118,812
[45] Date of Patent: Jun. 2, 1992

[54] PYRAZOLOAZOLE SERIES COUPLERS

[75] Inventors: Shigeki Yokoyama; Tadahisa Sato; Keizo Kimura; Nobuo Furutachi; Osamu Takahashi, all of Kanagawa, Japan

[73] Assignee: Fuji Photo Film Co., Ltd., Kanagawa, Japan

[21] Appl. No.: 549,667

[22] Filed: Jul. 6, 1990

Related U.S. Application Data

[63] Continuation of Ser. No. 130,502, Dec. 9, 1987, abandoned.

[30] Foreign Application Priority Data

Dec. 9, 1986 [JP] Japan .................. 61-292752
Aug. 6, 1987 [JP] Japan .................. 62-195188

[51] Int. Cl.$^5$ .............................. C07D 487/04
[52] U.S. Cl. .......................... 548/262.4; 548/251
[58] Field of Search .................... 548/262.4, 251

[56] References Cited

U.S. PATENT DOCUMENTS 2,891,862  6/1959  von Allan ................ 548/266
4,873,183  10/1989  Tachibana et al. ......... 430/550

FOREIGN PATENT DOCUMENTS 0119860  9/1984  European Pat. Off. ........ 548/262.4
0173256  3/1986  European Pat. Off. ........ 548/262.4
0284240  9/1988  European Pat. Off. ........ 548/262.4
0111036  7/1983  Japan ..................... 548/262.4
1261738  11/1986 Japan ..................... 548/266

Primary Examiner—David B. Springer
Attorney, Agent, or Firm—Sughrue, Mion, Zinn, Macpeak & Seas

[57] ABSTRACT

A pyrazoloazole series coupler having the following formula (I)

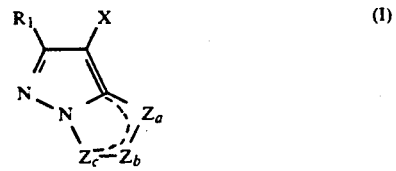

wherein
$R_1$ represents a substituent having a Hammett's substituent constant $\sigma_p$ of at least 0.6;
X represents a hydrogen atom or a group capable of being released by the coupling reaction with the oxidation product of an aromatic primary amine developing agent;
$Z_a$, $Z_b$ and $Z_c$ each represents =CH—,

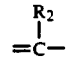

(wherein $R_2$ represents a hydrogen atom or a substituent), =N— or —NH—;
one of $Z_a$—$Z_b$ bond and $Z_b$—$Z_c$ bond is a double bond and the other is a single bond;
when $Z_b$—$Z_c$ is a carbon-carbon double bond, this $Z_b$—$Z_c$ may form a part of another aromatic ring;
$R_1$, $R_2$ or X may be a divalent linking group forming a dimer, or $R_1$ or $R_2$ may be a divalent linking group bonded to a polymer main chain to form a polymer, a silver halide photographic material which has at least one layer containing the coupler or a support and a method for processing a silver halide color photographic material with a developer containing an aromatic primary amine developing agent in the presence of the coupler.

8 Claims, 1 Drawing Sheet

PYRAZOLOAZOLE SERIES COUPLERS

This is a continuation of application Ser. No. 07/130,502 filed Dec. 9, 1987, now abandoned.

FIELD OF THE INVENTION

The present invention relates to a pyrazoloazole series coupler, a silver halide color photographic material and a method for forming a color images, more precisely, it relates to a new pyrazoloazole series coupler, a silver halide color photographic material containing the same and a method for forming a color image containing the same and a photographic material in the presence of the coupler, and still more precisely, it relates to a new pyrazoloazole series coupler into which an especially strong electron attractive group has been introduced, a silver halide color photographic material containing the same and a method for forming a color image of a silver halide color photographic material in the presence of the coupler.

BACKGROUND OF THE INVENTION

Hitherto, various 5-pyrazolone series couplers have been utilized as a magenta color image-forming coupler of a silver halide color photographic material. However, the magenta color image-forming dye to be formed by the coupling reaction with the 5-pyrazolone series coupler and the oxidation product of an aromatic primary amine developing agent has a harmful side-absorption near 430 nm in the short wavelength side of the main absorption, in addition to the main absorption, and the side-absorption causes a decrease in the sharpness of the magenta color formed to lower the color reproducibility of the color photographic material containing the coupler.

In order to eliminate such harmful side-absorption, various studies have been carried out for a long period of time in the field of photographic light-sensitive materials and, as a result, various magenta couplers have been proposed, including, for example, 1H-pyrazolo[1,5-b]benzimidazoles described in U.S. Pat. No. 3,061,432; 1H-pyrazolo[5,1-c]1,2,4-triazoles described in U.S. Pat. No. 3,725,067; 1H-imidazo[1,2-b]pyrazoles described in U.S. Pat. No. 4,500,630; 1-pyrazolo[1,5-b]-1,2,4-triazoles described in U.S. Pat. No. 4,540,654; 1H-pyrazolo[1,5-d]tetrazoles described in Japanese Patent Application (OPI) No. 33552/85 (the term "OPI" as used herein refers to a "published unexamined patent application"); 1H-pyrazolo[1,5-b]pyrazoles described in Japanese Patent Application (OPI) No. 43659/85, etc. The magenta dyes to be formed from these pyrazoloazole series magenta couplers have little of the above-mentioned harmful side-absorption and, in particular, the 1H-pyrazolo[5,1-c]-1,2,4-triazoles described in U.S. Pat. No. 3,725,067, the 1H-pyrazolo[1,5-b]-1,2,4-triazoles described in U.S. Pat. No. 4,540,654 and the 1H-pyrazolo[1,5-d]tetrazoles described in Japanese Patent Application (OPI) No. 33552/85 can form magenta dyes having sharp visible absorption spectra and therefore can provide magenta color image-forming dyes with an improved hue.

However, it is still desired to obtain such couplers which are able to provide sharper absorption spectra and which are able to form sharper colors than the magenta dyes formed from the thus-improved pyrazoloazole series magenta couplers mentioned above.

In addition, since the molecular extinction coefficient of the magenta dye formed from the pyrazoloazole series magenta coupler is at most $6 \times 10^4 \, l \cdot mol^{-1} \cdot cm^{-1}$, it is desired to obtain other couplers capable of providing a greater molecular extinction coefficient. Dyes having a greater molecular extinction coefficient can provide the desired optical density even when they are used in a small amount. Therefore, the silver halide photographic material containing the coupler providing a greater molecular extinction coefficient can have a thin film thickness, whereby silver halide photographic materials would have improved sharpness, would be suitable for more rapid processing and, additionally, would be less expensive.

SUMMARY OF THE INVENTION

The present inventors earnestly and repeatedly conducted research to develop couplers that satisfy the above-mentioned objectives with regard to the conventional pyrazoloazole series magenta couples and, as a result, have found that the introduction of an especially strong electron attractive group into a substituent of a pyrazoloazole coupler is effective in forming a dye from the coupler which has a sharper visible absorption spectrum and provides a sharper hue and has a higher molecular extinction coefficient of up to $9 \times 10^4 \, l \cdot mol^{-1} \cdot cm^{-1}$.

Moreover, the present inventors have further found that the introduction of an especially strong electron attractive group into a substituent of a pyrazoloazole coupler causes a remarkable shift of the maximum absorption wavelength to a deep color so that the resulting pyrazoloazole coupler may provide a new cyan (or blue) image-forming dye having a maximum absorption wavelength of more than 600 nm, provided that the pyrazoloazole skeleton and the especially strong electron attractive group are properly selected, while the dye formed from a conventional pyrazoloazole coupler is a magenta (or red or bluish violet) dye having a maximum absorption wavelength within the range of from about 510 nm to about 570 nm.

Accordingly, a first object of the present invention is to provide a new pyrazoloazole series magenta or cyan coupler capable of providing a sharp color with a sharp visible absorption spectrum, a silver halide color photographic material containing the coupler which has an improved hue, as well as a method of forming a color image using a silver halide color photographic material, which, in the presence of the coupler, has an improved hue.

A second object of the present invention is to provide a new pyrazoloazole series magenta or cyan coupler which has a high molecular extinction coefficient, so that a desired optical density may be obtained even when the coupler is used in a small amount, a silver halide color photographic material containing the coupler, and a method for forming a color image using a silver halide color photographic material in the presence of the coupler.

These objects of the present invention can be achieved by a new pyrazoloazole series coupler as represented by the following general formula (I), a silver halide photographic material which has at least one layer containing the coupler on a support, and a method for processing a silver halide color photographic material with a developer containing an aromatic primary amine developing agent in the presence of the coupler:

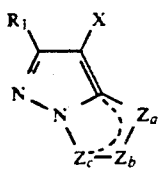 (I)

wherein $R_1$ represents a substituent having a Hammett's substituent constant $\sigma_p$ of at least 0.6;

X represents a hydrogen atom or a group capable of being released by the coupling reaction with the oxidation product of an aromatic primary amine developing agent;

Za, Zb and Zc each represents =CH—,

(wherein $R_2$ represents a hydrogen atom or a substituent), =N— or —NH—;

one of Za—Zb bond and Zb—Zc bond is a double bond and the other is a single bond;

when Zb—Zc is a carbon-carbon double bond, this Zb—Zc may form a part of another aromatic ring;

$R_1$, $R_2$ or X may be a divalent linking group forming a dimer, or $R_1$ or $R_2$ may be a divalent linking group bonded to a polymer main chain to form a polymer.

DETAILED DESCRIPTION OF THE INVENTION

Figure 1:
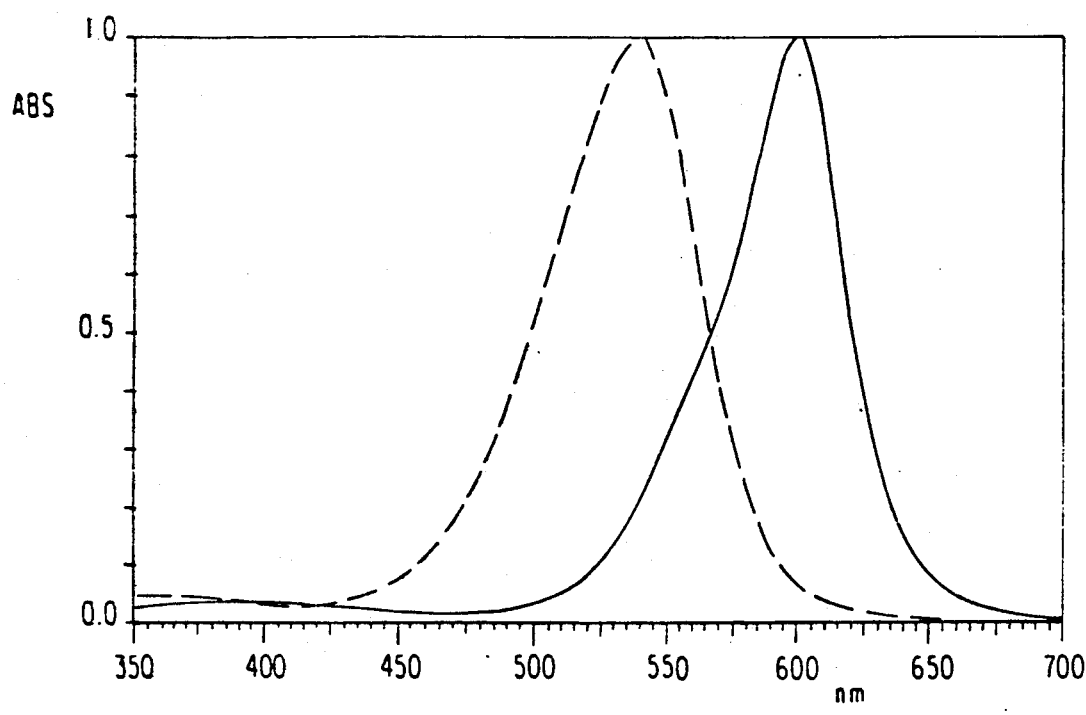
In FIG. 1, the solid line shows the visible absorption spectrum of the image-forming cyan dye (D-1) formed from the pyrazoloazole series cyan coupler compound No. 1 of the present invention in the silver halide color photographic material of Example 1. The dashed line shows the visible absorption spectrum of the magenta dye (D-2) formed from the comparative pyrazoloazole series magenta coupler (C-2) in the material of Example 1.

The new pyrazoloazole series magenta or cyan couplers of the present invention, which have an especially strong electron attractive group, are explained in detail hereinafter.

The substituent represented by $R_1$ in formula (I) preferably has a Hammett's substituent constant $\sigma_p$ of from 0.6 to 2.0 and more preferably from 0.6 to 1.0.

The pyrazoloazole series magenta or cyan couplers of formula (I) are preferably those represented by formulae (II), (III), (IV), (V), (VI) and (VII)

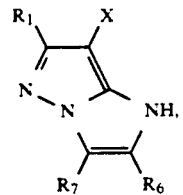 (II)

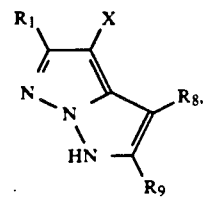 (III)

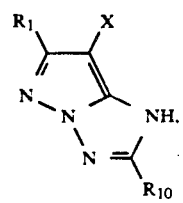 (IV)

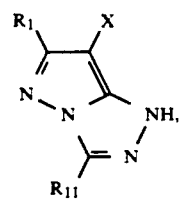 (V)

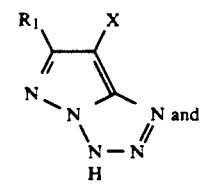 (VI)

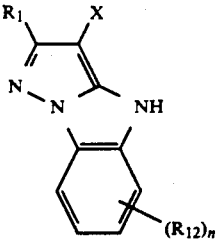 (VII)

In formulae (II), (III), (IV), (V), (VI) and (VII), $R_1$ and X are as defined above, $R_6$, $R_7$, $R_8$, $R_9$, $R_{10}$, $R_{11}$ and $R_{12}$ each represents a hydrogen atom or a substituent, and n is an integer of 1 to 4.

The pyrazoloazole series magenta or cyan couplers of present invention are more preferably those represented formula (IV), (V) or (VI); and still more preferably those represented by formula (IV).

Examples of groups shown by $R_6$, $R_7$, $R_8$, $R_9$, $R_{10}$, $R_{11}$, and $R_{12}$ in formulae (II) to (VII) described above include a hydrogen atom, a halogen atom, a saturated or unsaturated aliphatic or alicyclic hydrocarbon group, an aryl group, a heterocyclic group, a cyano group, an alkoxy group, an aryloxy group, an acylamino group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclic oxy group, an acyloxy group, an acylaminooxy group, a silyloxy group, an aryloxycarbonylamino group, an imido group, a heterocyclic thio group, a sulfinyl group, a phosphonyl group, an aryloxycarbonyl group, an acyl group, a nitro group, a trialkylammonium group, a triarylammonium group, a dialkylsulfonium, a diarylsulfonium, etc.

X may represent a hydrogen atom, a halogen atom, a carboxyl group or a group to be bonded to the carbon atom at the coupling position via an oxygen atom, nitrogen atom, carbon atom or sulfur atom, which can be released by coupling.

$R_1$, $R_6$ to $R_{12}$ or X may be a divalent linking group to form a bis-form, or any of $R_1$ and $R_6$ to $R_{12}$ may be a divalent linking group bonded to a polymer main chain to form a polymer.

More specifically, examples of $R_6$, $R_7$, $R_8$, $R_9$, $R_{10}$, $R_{11}$, $R_{12}$ are a hydrogen atom, a halogen atom (e.g., a chlorine atom, a bromine atom, etc.), a saturated or unsaturated aliphatic or alicyclic hydrocarbon group preferably having 1 to 32 carbon atoms (e.g., a straight chain or branched alkyl group, an aralkyl group, an alkenyl group, an alkynyl group, a cycloalkyl group, and a cycloalkenyl group, each of which may be substituted by a substituent which is connected thereto through an oxygen atom, a nitrogen atom, a sulfur atom, or a carbonyl group, a hydroxy group, an amino group, a nitro group, a carboxy group, a cyano group, or a halogen atom, such as a methyl group, a propyl group, a t-butyl group, a trifluoromethyl group, a tridecyl group, a 2-methanesulfonylethyl group, a 3-(3-pentadecylphenoxy)propyl group, a 3-{4-{2-[4-(4-hydroxyphenylsulfonyl)phenoxyl]dodecanamido}phenyl}propyl group, a 2-ethoxytridecyl group, a trifluoromethyl group, a cyclopentyl group, a 3-(2,4-di-t-amylphenoxy)propyl group, a β-carboxyvinyl group, a β,β-dicyanovinyl group, etc.), an aryl group (e.g., a phenyl group, a 4-t-butylphenyl group, a 2,4-di-t-amylphenyl group, a 4-tetradecanamidophenyl group, etc.), a heterocyclic group (e.g., a 5- to 7-membered heterocyclic ring having at least one of N, O and S atoms, such as a 2-furyl group, a 2-thienyl group, 2-pyrimidinyl group, a 2-benzothiazolyl group, etc.), a cyano group, an alkoxy group (e.g., a methoxy group, an ethoxy group, a 2-methoxyethoxy group, a 2-dodecylethoxy group, a 2-methanesuflonylethoxy group, etc.), an aryloxy group (e.g., a phenoxy group, a 2-methylphenoxy group, a 4-t-butylphenoxy group, etc.), an acylamino group (e.g., an acetamido group, a benzamido group, a tetradecanamido group, an α-(2,4-di-t-amylphenoxy)-butylamido group, a γ-3-t-butyl-4-hydroxyphenoxy)-butylamido group, an α-{4-(4-hydroxyphenylsulfonyl)-phenoxy}decanamido group, etc.), an anilino group (e.g., a phenylamino group, a 2-chloroanilino group, a 2-chloro-5-tetradecanamidoanilino group, a 2-chloro-5-dodecyloxycarbonylanilino group, an N-acetylanilino group, a 2-chloro-5-{α-(3-t-butyl-4-hydroxyphenoxy)-dodecanamido}anilino group, etc.), a ureido group (e.g., a phenylureido group, a methylureido group, an N,N-dibutylureido group, etc.), a sulfamoylamino group (e.g., an N,N-dipropylsulfamoylamino group, an N-methyl-N-decylsulfamoylamino group, etc.), an alkylthio group (e.g., a methylthio group, an octylthio group, a tetradecylthio group, a 2-phenoxyethylthio group, a 3-phenoxypropylthio group, a 3-(4-t-butyl-phenoxy)propylthio group, etc.), an arylthio group (e.g., a phenylthio group, a 2-butoxy-5-t-octylphenylthio group, a 3-pentadecylphenylthio group, a 2-carboxyphenylthio group, a 4-tetradecanamidophenylthio group, etc.), an alkoxycarbonylamino group (e.g., a methoxycarbonylamino group, a tetradecyloxycarbonylamino group, etc.), a sulfonamido group (e.g., a methanesulfonamido group, a hexadecanesulfonamido group, a benzenesulfonamido group, a p-toluenesulfonamido group, an octadecanesulfonamido group, a 2-methyloxy-5-t-butylbenzenesulfonamido group, etc.), a carbamoyl group (e.g., an N-ethylcarbamoyl group, an N,N-dibutylcarbamoyl group, an N-(2-dodecyloxyethyl)carbamoyl group, an N-methyl-N-dodecylcarbamoyl group, an N-{3-(2,4-di-t-amylphenoxy)propyl}carbamoyl group, etc.), a sulfamoyl group (e.g., an N-ethylsulfamoyl group, an N,N-dipropylsulfamoyl group, an N-(2-dodecyloxyethyl)sulfamoyl group, an N-ethyl-N-dodecylsufamoyl group, an N,N-diethylsulfamoyl group, etc.), a sulfonyl group (e.g., a methanesulfonyl group, an octanesulfonyl group, a benzenesulfonyl group, a toluenesulfonyl group, etc.), an alkoxycarbonyl group (e.g., a methoxycarbonyl group, a butyloxycarbonyl group, a dodecyloxycarbonyl group, an octadecyloxycarbonyl group, etc.), a heterocyclic oxy group (wherein the heterocyclic group preferably is a 5- to 7-membered heterocyclic ring having at least one of N, O and S atoms, such as a 1-phenyltetrazole-5-oxy group, a 2-tetrahydroxypyranyloxy group, etc.), an acyloxy group (e.g., an acetoxy group, etc.), an acylaminooxy group (e.g., an acetylaminooxy group, a benzoylaminooxy group, etc.), a silyloxy group (e.g., a trimethylsilyloxy group, a dibutylmethylsilyloxy group, etc.), an aryloxycarbonylamino group (e.g., a phenoxycarbonylamino group, etc.), an imido group (e.g., an N-succinimido group, an N-phthalimido group, a 3-octadecenylsuccinimido group, etc.), a heterocyclic thio group (wherein the heterocyclic group preferably is a 5- to 7-membered heterocyclic ring having at least one of N, O and S atoms, such as a 2-benzothiazolylthio group, a 2,4-di-phenoxy-1,3,5-triazole-6-thio group, a 2-pyridylthio group, etc.), a sulfinyl group (e.g., a dodecanesulfinyl group, a 3-pentadecylphenylsulfinyl group, a 3-phenoxypropylthio group, etc.), a phosphonyl group (e.g., a phenoxyphosphonyl group, an octyloxyphosphonyl group, a phenylphosphonyl group), an aryloxycarbonyl group (e.g., a phenoxycarbonyl group, etc.), an acyl group (e.g., an acetyl group, a 3-phenylpropanoyl group, a benzoyl group, a 4-dodecyloxybenzoyl group, etc.), etc.

The substituents for $E_6$ to $R_{11}$ in formulae (II) to (V) are preferably selected from the above-mentioned groups such that the sum of the $\sigma_p$ values of $R_1$, $R_6$ and $R_7$ in formula (II) is within the range from 0.60 to 2.00; the sum of the $\sigma_p$ values of $R_1$, $R_8$ and $R_9$ in formula (III) is within the range from 0.60 to 2.00; the sum of the $\sigma_p$ values of $R_1$ and $R_{10}$ in formula (IV) is within the range of from 0.60 to 2.00; or the sum of the $\sigma_p$ values of $R_1$ to $R_{11}$ in formula (V) is within the range from 0.60 to 2.00.

Preferred examples of groups having a Hammett's substituent constant $\sigma_p$ value of from 0.6 to 2.00 are a cyano group, a nitro group, a trialkylammonium group (e.g., a trimethylammonium group, a triethylammonium group, a tributylammonium group, a trioctylammonium group, a tridecylammonium group, a dihydroxyethylmethylammonium group, etc.), a triarylammonium group (e.g., a triphenylammonium group, a tritolylammonium group, etc.), a dialkylsulfonium group (e.g., a dimethylsulfonium group, a diethylsulfonium group, etc.), a diarylsulfonium group (e.g., a diphenylsulfonium group, etc.), a perfluoroalkylsulfinyl group (e.g., a trifluoromethylsulfinyl group, a pentafluoroethylsulfinyl group, a heptafluoropropylsulfinyl group, a perfluorooctylsulfinyl group, etc.), an ω-hydroperfluoroalkylsulfinyl group (e.g., an ω-hydroperfluorooctylsulfinyl group, an ω-hydroperfluorododecylsulfinyl group, etc.), an alkylsulfonyl group (e.g., methylsulfonyl group, difluoromethylsulfonyl group, a trifluoromethylsulfonyl group, a dichloromethylsulfonyl group, an ethylsulfonyl group, a propylsulfonyl group, an octylsulfonyl group, a decylsulfonyl group, a pentafluoroethylsulfonyl group, a heptafluoropropylsulfonyl group, a perfluorooctylsulfonyl group, an ω-hydroperfluorooctylsulfonyl group, etc.), an arylsulfonyl group (e.g., a phenylsulfonyl group, a tolylsulfonyl group, a pentafluorophenylsulfonyl group, etc.), a β-carboxyvinyl group, a β,β-dicyanovinyl group, etc.

These examples are further described, for example, in C. Hansch et al., *Substituent Constants for Correlation Analysis in Chemistry and Biology*, John Wiley & Sons, New York (1979), C. Hansch et al., *Journal of Medicinal Chemistry*, vol. 16, pp. 1207–1216 (1973), C. Hansch et al., ibid, Vol. 20, pp. 304–306 (1977), etc.

However, it is not unusual that different values are reported by different reporters for the same substituent, and in that case it is preferred to use values described in the last two references (both, C. Hansch et al) listed above. Further with respect to substituents which are not described in the above references, measurement can be performed in accordance with the definition described in L. P. Hammett, *Physical Organic Chemistry*, McGraw-Hill (1970).

X, more specifically, may represent a hydrogen atom, a halogen atom (e.g., a chlorine atom, a bromine atom, an iodine atom), a carboxyl group, a group that can be and is bonded directly to the formula (I) structure via an oxygen atom (e.g., an acetoxy group, a propanoyloxy group, a benzoyloxy group, a 2,4-dichlorobenzoyloxy group, an ethoxyoxaloyloxy group, a pyruvinyloxy group, a cinnamoyloxy group, a phenoxy group, a 4-cyanophenoxy group, a 4-methanesulfonamidophenoxy group, a 4-methanesulfonylphenoxy group, an α-naphthoxy group, a 3-pentadecylphenoxy group, a benzyloxycarbonyloxy group, an ethoxy group, a 2-cyanoethoxy group, a benzyloxy group, a 2-phenethyloxy group, a 2-phenoxyethoxy group, a 5-phenyltetrazolyloxy group, a 2-benzothiazolyloxy group, etc.), a group that can be and is bonded directly to the formula (I) structure via a nitrogen atom (e.g., a benzenesulfonamido group, an N-ethyltoluenesulfonamido group, a heptafluorobutanamido group, a 2,3,4,5,6-pentafluorobenzamido group, an octanesulfonamido group, a p-cyanophenylureido group, an N,N-diethylsulfamoylamino group, a 1-piperidyl group, a 5,5-dimethyl-2,4-dioxo-3-oxazolidinyl group, a 1-benzyl-ethoxy-3-hydantoinyl group, a 2H-1,1-di-oxo-3-(2H)-oxo-1,2-benzisothiazolyl group, a 2-oxo-1,2-dihydro-1-pyridinyl group, an imidazolyl group, a pyrazolyl group, a 3,5-diethyl-1,2,4-triazol-1-yl group, a 5- or 6-bromo-benzotriazol-1-yl group, a 5-methyl-1,2,3,4-triazol-1-yl group, a benzimidazolyl group, a 4-methoxyphenylazo group, a 4-pivaloylamino-ohenylazo group, a 2-hydroxy-4-propanoylphenylazo group, etc.), a group that can be and is bonded directly to the formula (I) structure via a sulfur atom (e.g., a phenylthio group, a 2-carboxyphenylthio group, a 2-methoxy-5-t-octylphenylthio group, a 4-methanesulfonylphenylthio group, a 4-octanesulfonamidophenylthio group, a benzylthio group, a 2-cyanoethylthio group, a 1-ethoxycarbonyltridecylthio group, a 5-phenyl-2,3,4,5-tetrazolylthio group, a 2-benzothiazolyl group, a thiocyano group, an N,N-diethylthiocarbonylthio group, a dodecyloxythiocarbonylthio group, etc.), or a group that can be and is bonded directly to the formula (I) structure via a carbon atom (e.g., a triphenylmethyl group, a hydroxymethyl group, an N-morpholinomethyl group, a group of formula

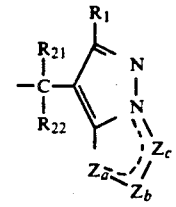

in which $R_{21}$ and $R_{22}$ each represents a hydrogen atom, an alkyl group, an aryl group or a heterocyclic group and $R_1$, $Z_a$, $Z_b$ and $Z_c$ each has the same meaning as in formula (I) above, etc.), etc.

In particular, the groups that can be and are bonded directly to the formula (I) structure via an oxygen atom or a nitrogen atom are especially preferable as X among these groups.

As X, groups which are known as coupling-releasable groups can be used without any limitations on their formula or structure.

In the present invention, when $R_1$, $R_6$, $R_7$, $R_8$, $R_9$, $R_{10}$, $R_{11}$, $R_{12}$ and X each represents an alkyl group or a group containing an alkyl group (such as an alkoxy group, an alkylthio group, an alkoxycarbamoyl group, an alkoxycarbonyl group, etc.), the number of carbon atoms in the alkyl group or alkyl moiety is generally from 1 to 50, preferably from 1 to 40, and more preferably from 1 to 32; and the same carbon atom number ranges apply to the number of carbon atoms in an acyl group, in the case when a substituent represents an acyl group.

In formulae (II) through (VII); any of $R_1$, $R_6$ to $R_{12}$ and X may be a divalent linking group to form a dimer (bis-form) via the linking group.

The divalent groups of $R_1$, $R_6$ to $R_{12}$ and X which form in a bis-form of formulae (II) through (VII) are mentioned in greater detail below. $R_1$ and $R_6$ to $R_{12}$ may be a substituted or unsubstituted alkylene group (such as a methylene group, an ethylene group, a 1,10-decylene group, etc.), a substituted or unsubstituted alkyleneoxyalkylene group (such as —CH$_2$CH$_2$—O—CH$_2$CH$_2$—, etc.); a substituted or unsubstituted phenylene group (such as a 1,4-phenylene group, a 1,3-phenylene group,

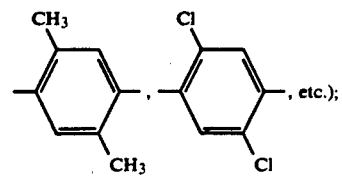

, etc.);

—NHCO—L$_1$—CONH— (in which L$_1$ represents a substituted or unsubstituted alkylene group or a substituted or unsubstituted phenylene group, such as —NHCOCH₂CH₂CONH—,

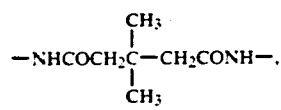

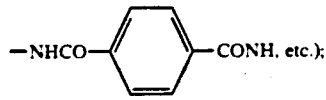

—S—L₂—S— (in which L₂ represents a substituted or unsubstituted alkylene group, such as —S—CH₂CH₂—S—,

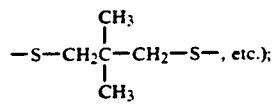

and X may be the above-mentioned releasable group bonded to the divalent linking group.

The pyrazoloazole series magenta or cyan couplers represented by formulae (II) to (VII) may be in the form of a polymer which is linked with the polymer main chain via a divalent linking group of any of $R_1$ and $R_6$ to $R_{12}$.

Such divalent linking group may comprise a combination of groups selected from an alkylene group (which is a substituted or unsubstituted alkylene, such as methylene group, an ethylene group, 1,10-decylene group, etc.); a substituted or unsubstituted alkyleneoxyalkylene group (such —CH₂CH₂OCH₂CH₂—, etc.); a substituted or unsubstituted phenylene group (such as a 1,4-phenylene group, a 1,3-phenylene group,

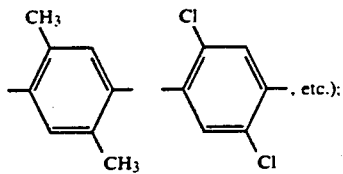

—NHCO—; —CONH—; —O—; —OCO—; and an aralkylene group (e.g.,

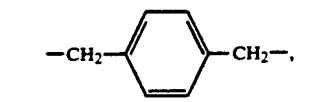

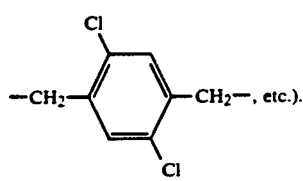

Preferred divalent linking groups for linking with a polymer chain are as follows:

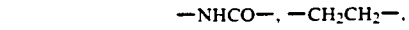

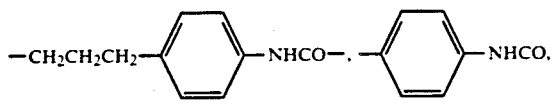

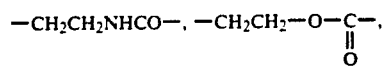

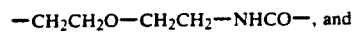

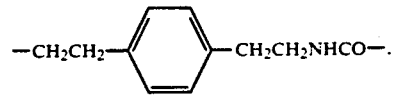

In the case when the pyrazoloaxole series magenta or cyan couplers of formulae (II) to (VII) are polymers, such polymer couplers themselves and the use thereof may be the same as those described in U.S. Pat. No. 4,540,654.

Concretely, the monomers containing the moiety of any of formulae (II) to (VII) can be homo-polymerized to form polymers or, alternatively, they can be copolymerized with a non-coloring ethylenic monomer which is not coupled with the oxidation product of an aromatic primary amine developing agent to form copolymers.

Examples of the non-coloring ethylenic monomer which is not coupled with the oxidation product of an aromatic primary amine developing agent includes acrylic acid, α-chloroacrylic acid, α-alkylacrylic acids (e.g., methacrylic acid, etc.), as well as esters and amides derived from such acrylic acid compounds (e.g., acrylamide, n-butylacrylamide, t-butylacrylamide, diacetoneacrylamide, methacrylamide, methyl acrylate, ethyl acrylate, n-propyl acrylate, n-butyl acrylate, t-butyl acrylate, iso-butyl acrylate, 2-ethylhexyl acrylate, n-octyl acrylate, lauryl acrylate, methyl methacrylate, ethyl methacrylate, n-butyl methacrylate, β-hydroxyethyl methacrylate, etc.), methylene-dibis-acrylamide, vinyl esters (e.g., vinyl acetate, vinyl propionate, vinyl laurate, etc.), acrylonitrile, methacrylonitrile, aromatic vinyl compounds (e.g., styrene and derivatives thereof, vinyltoluene, divinylbenzene, vinylacetophenone, sulfostyrene, etc.), itaconic acid, citraconic acid, crotonic acid, vinylidene chloride, vinyl alkyl ethers (e.g., vinyl ethyl ether, etc.), maleic acid, maleic anhydride, maleic acid esters, N-vinyl-2-pyrrolidone, N-vinylpyridine, 2- and 4-vinylpyridine, etc.

Two or more of these non-coloring ethylenic unsaturated monomers can be used in combination. For instance, there may be mentioned combinations of n-butyl acrylate and methyl acrylate; styrene and methacrylic acid; methacrylic acid and acrylamide; methyl acrylate and diacetoneacrylamide; etc.

As is well known in the field of polymer color couplers, the non-coloring ethylenic unsaturated monomer to be copolymerized with the water-insoluble solid monomers coupler may be so selected that the physical properties and/or the chemical properties of the copolymer formed, such as the solubility, the compatibility with binders of photographic colloid compositions (such as gelatin), the flexibility, the thermal stability, etc., can conveniently be influenced by the non-coloring comonomer.

The polymer couplers for use in the present invention may either be soluble or insoluble in water and, in particular, polymer coupler latexes are especially preferred among these polymer couplers.

Specific examples of typical magenta or cyan couplers of the present invention are shown below, which, however, should not be construed as being limiting upon the scope of the present invention.

Compound No. 1

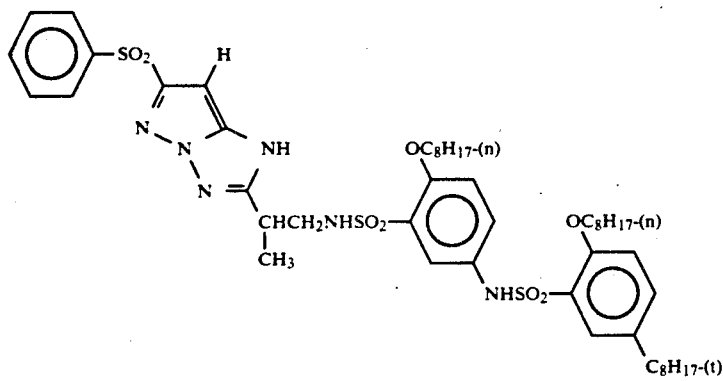

Compound No. 2

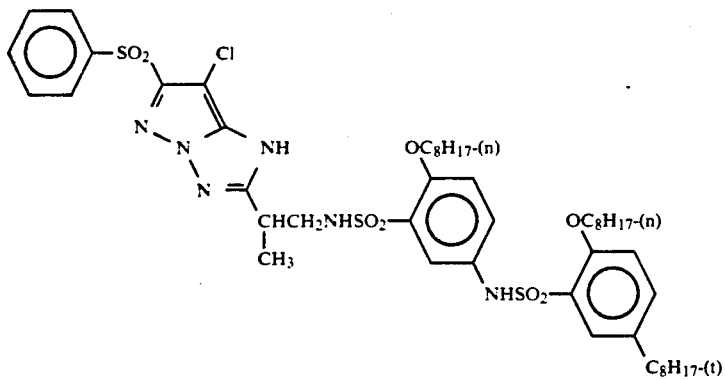

Compound No. 3

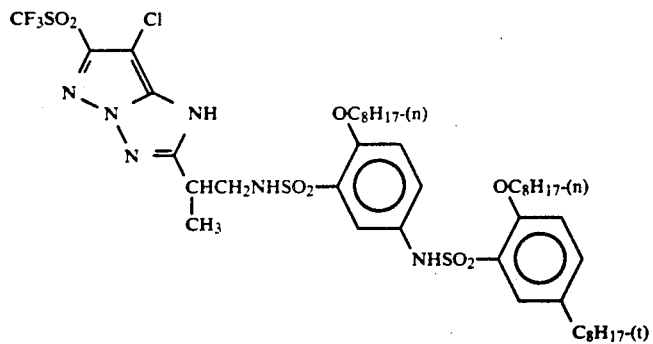

Compound No. 4

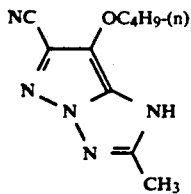

Compound No. 6

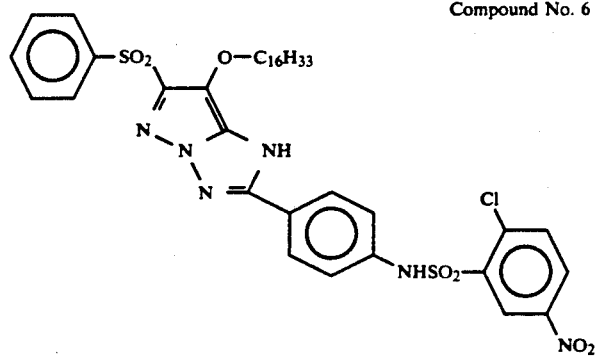

-continued
Compound No. 7
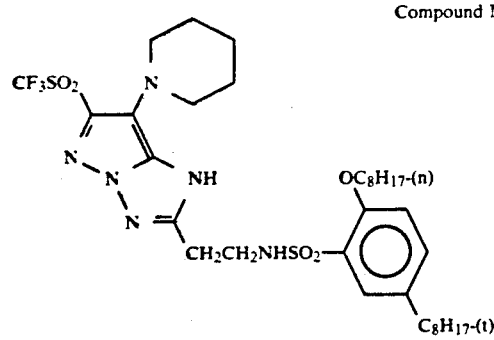
Compound No. 8
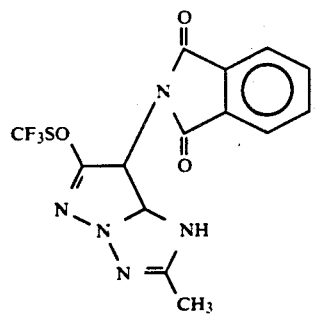
Compound No. 9
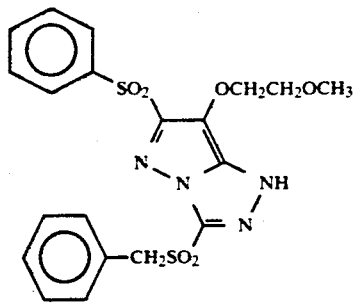
Compound No. 10
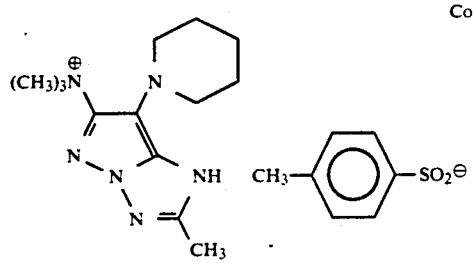
Compound No. 11
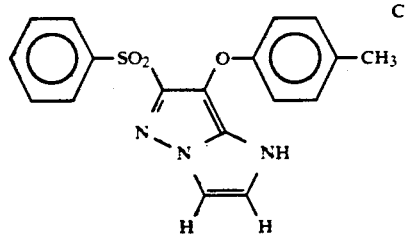
Compound No. 12
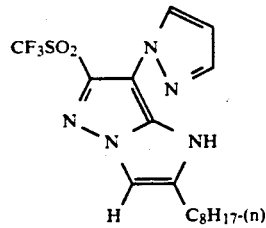
Compound No. 13
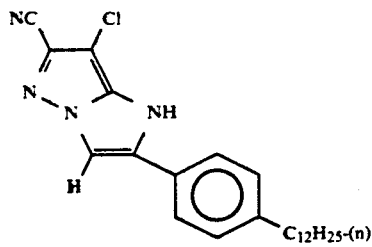
Compound No. 15
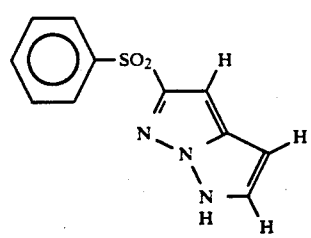
Compound No. 16
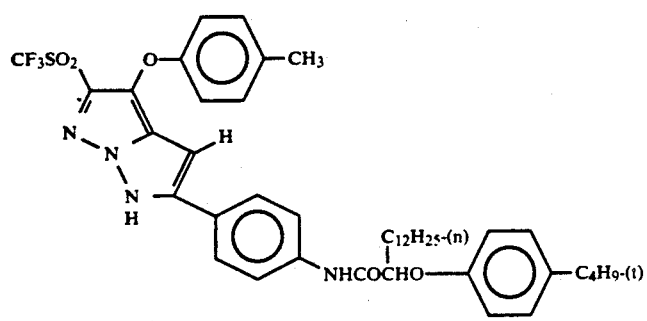

-continued
Compound No. 17
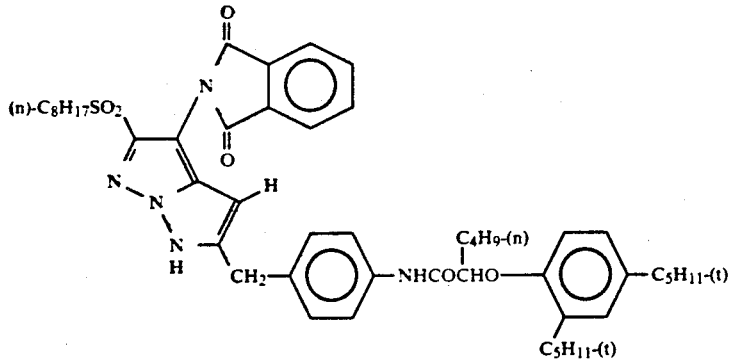
Compound No. 18
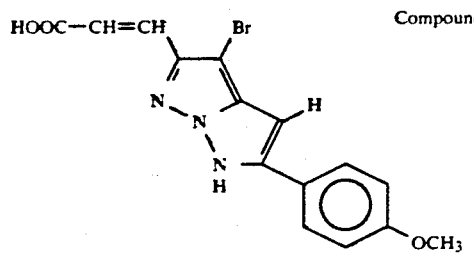
Compound No. 19
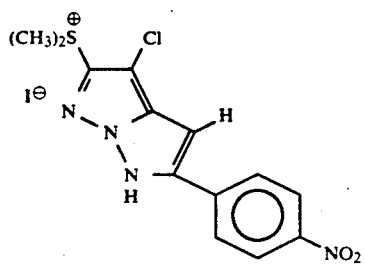
Compound No. 20
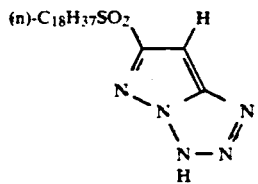
Compound No. 21
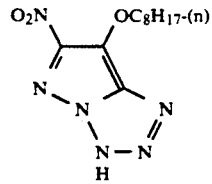
Compound No. 22
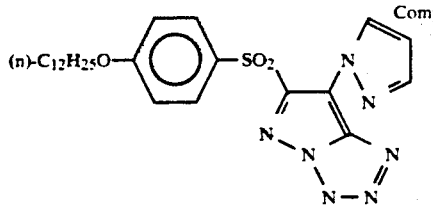
Compound No. 23
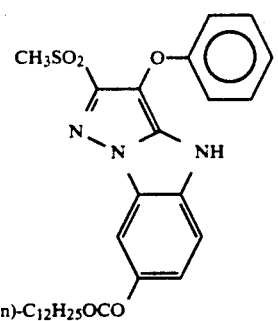
Compound No. 24
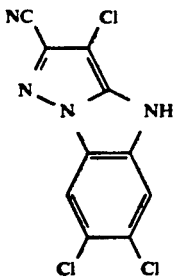
Compound No. 25
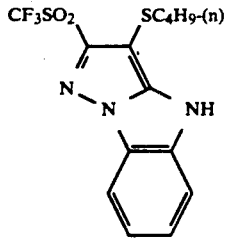
Compound No. 26
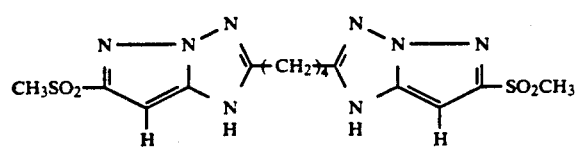

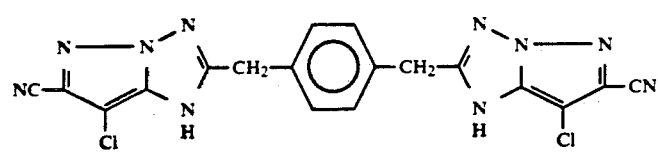
Compound No. 27
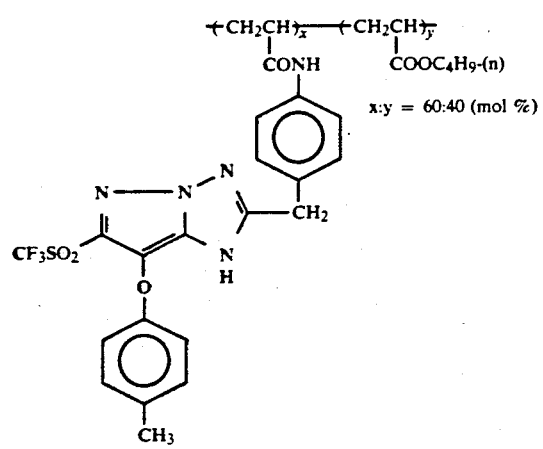
Compound No. 28
x:y = 60:40 (mol %)
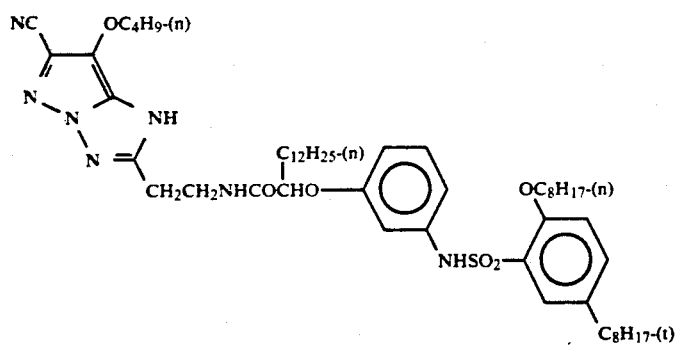
Compound No. 29
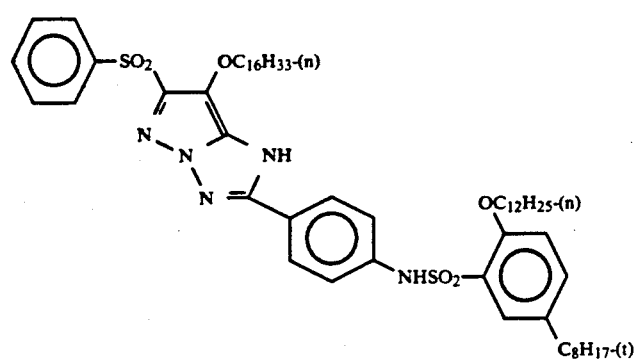
Compound No. 30

-continued
Compound No. 31
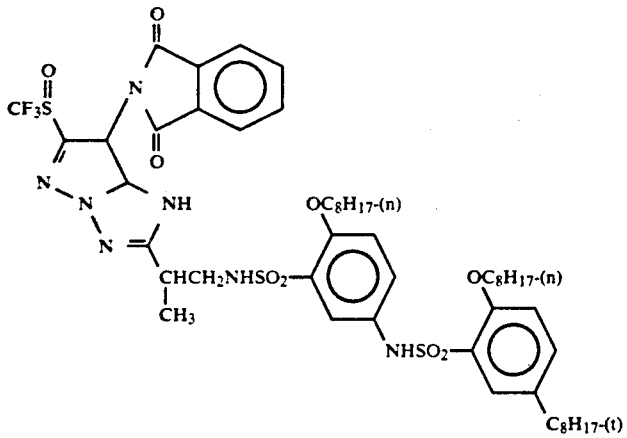
Compound No. 32
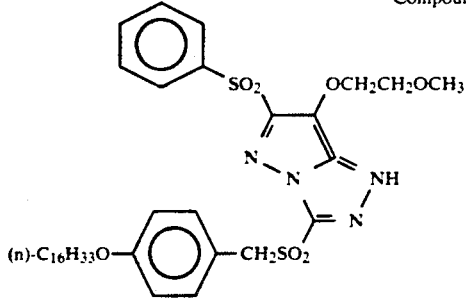
Compound No. 33
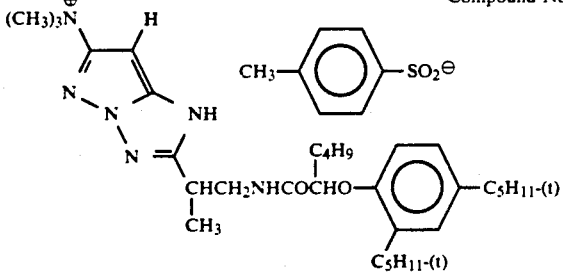
Compound No. 34
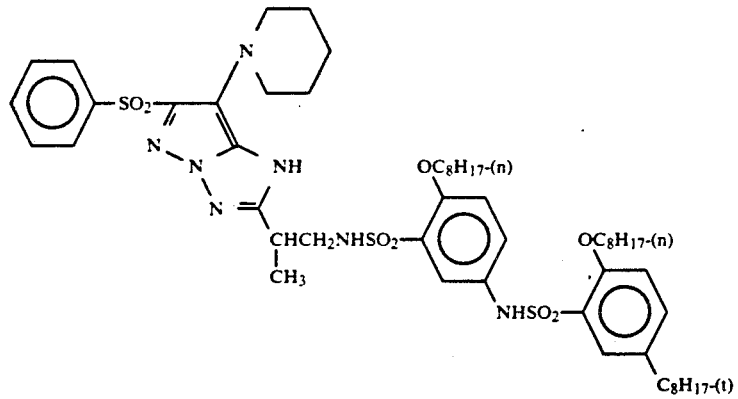
The Hammett's substituent constant $\sigma_p$ of the substituents in the above-mentioned couplers are shown below.
| Substituent | $\sigma_p$ |
| --- | --- |
| —SO$_2$CH$_3$ | 0.72 |
| —NO$_2$ | 0.78 |
| —SO$_2$CF$_3$ | 0.93 |
| —SO$_2$—C$_6$H$_5$ | 0.70 |
-continued
| Substituent | $\sigma_p$ |
| --- | --- |
| —CHCH$_2$NHSO$_2$— (with OC$_8$H$_{17}$-(n), OC$_8$H$_{17}$-(n), NHSO$_2$—C$_8$H$_{17}$-(t)) | −0.15 |
| —CN | 0.66 |

-continued

| Substituent | $\sigma_p$ |
|---|---|
| 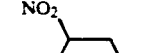 (2,4-dinitrotolyl) | 0.30 |
| —SOCF$_3$ | 0.69 |
| —N$^⊕$(CH$_3$)$_3$ | 0.82 |
| —CH$_3$ | −0.17 |
| —CH=CH—COOH | 0.90 |
| —S$^⊕$(CH$_3$)$_2$ | 0.90 |

The pyrazoloazole series magenta or cyan couplers of formula (I) of the present invention can be produced by selecting an appropriate method from the methods for producing various kinds of pyrazoloazoles as described, for example, in U.S. Pat. Nos. 3,061,432, 3,725,067, 4,500,630 and 4,540,654, British Patent 1,334,515, Japanese Patent Application (OPI) Nos. 33552/85 and 43659/85 and Japanese Patent Application No. 93098/86 incorporated herein by reference.

Concrete examples of methods for making pyrazoloazole series magenta or cyan couplers of the present invention are mentioned below. Unless otherwise specified, all parts, percents, and ratios are by weight.

SYNTHESIS EXAMPLE 1

Synthesis of Compound No. 1

Synthesis Route:

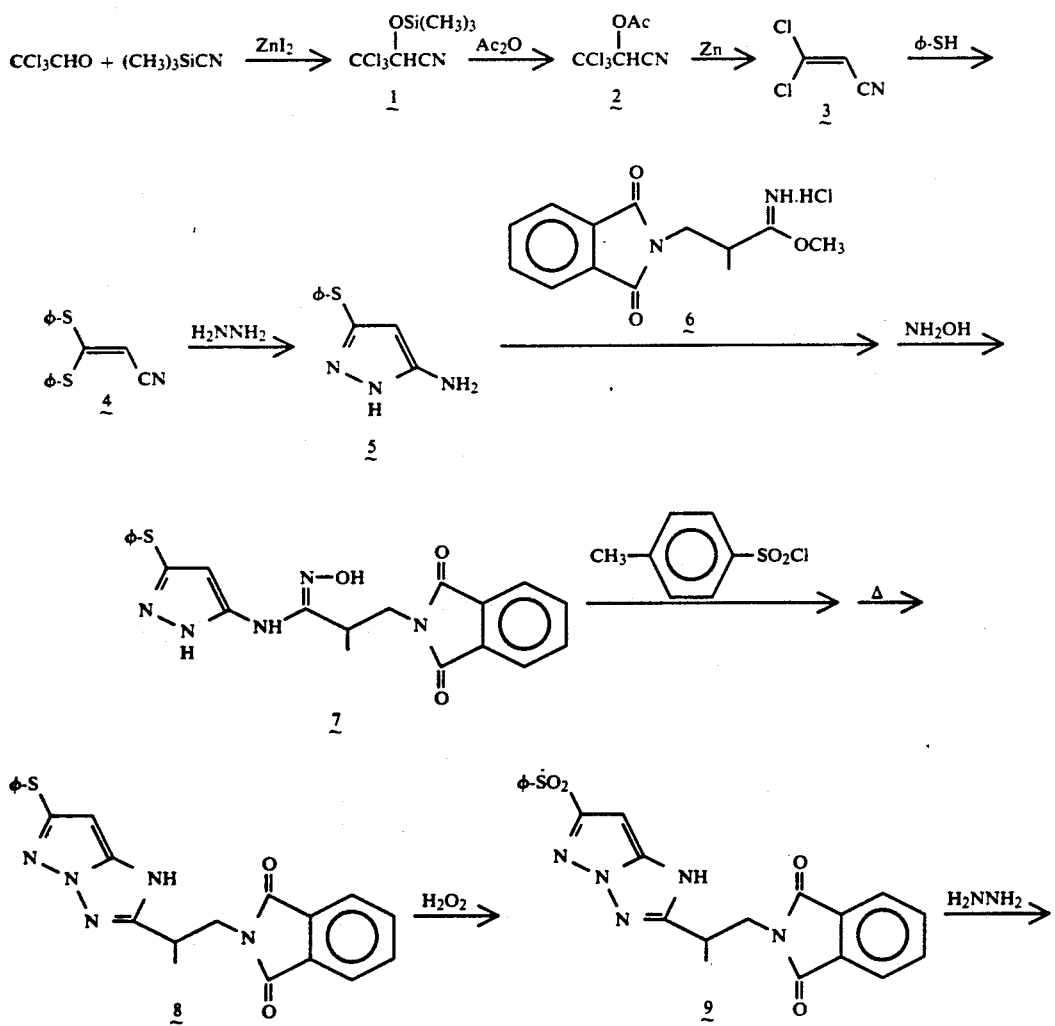

-continued
Synthesis Route:

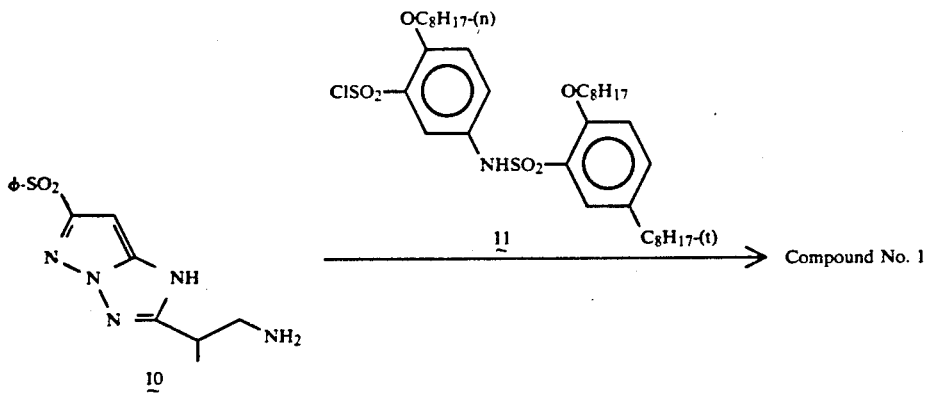

Synthesis of Intermediate (1)

116 g (0.79 mol) of chloral (a commercial chemical reagent), 24 g (0.075 mol) of zinc iodide and one liter of methylene dichloride were added to a 2 liter three-neck flask provided with a dropping funnel and a a stirrer and stirred at room temperature. Next, the contents were cooled to 8° to 10° C. and, while stirring, 105 ml (0.75 mol) of trimethylsilyl nitrile (a commercial chemical reagent) was dropwise added thereto within 30 minutes. The contents gradually changed from pink to brown. After the dropwise addition, the reaction mixture was continuously stirred for an additional 3 hours at room temperature. Then the insoluble materials were separated by filtration followed by distillation under reduced pressure.

The $^1$H-NMR spectrum (solvent CCl$_4$) of the thus-obtained liquid revealed $\delta = 0.50$ ppm (belonging to —Si(CH$_3$)$_3$ of Intermediate (1)), $\delta = 5.0$ ppm (belonging to the methine of the same) and $\delta = 5.4$ ppm (belonging to methylene dichloride). From the NMR integral strength ratio, the content of Intermediate (1) was 69.1 wt %, the yield thereof was 173 g and the yield percentage (productivity) thereof was 93%.

Synthesis of Intermediate (2)

170 g (0.69 mol) of Intermediate (1) containing 76 g of methylene chloride was put in a one liter three-neck flask provided with a reflux condenser and a stirrer, and 354 ml of acetic anhydride was further added thereto and stirred with heating at the external temperature of from 125° to 130° C. for 9 hours. After cooling to room temperature, the insoluble materials were separated off by filtration. After distillation under reduced pressure, the resulting liquid was subjected to column chromatography with silica-gel as a stationary phase and chloroform as a mobile phase. After further distillation under reduced pressure, the liquid thus treated was evaporated with a vacuum pump at 100° C. to remove the volatile component.

The $^1$H-NMR spectrum (solvent: CCl$_4$) of the liquid thus obtained revealed $\delta = 2.1$ ppm (belonging to acetic anhydride) and $\delta = 2.3$ ppm (belonging to the methine of Intermediate (2)). From the NMR integral strength ratio, the content of Intermediate (2) was 95.4 wt %, the yield thereof was 98.1 g, and yield percentage thereof was 66%.

Synthesis of Intermediate (3)

98.1 g (0.45 mol) of Intermediate (2) containing 4.5 g of acetic anhydride was put in a 2 liter three-neck flask provided with a stirrer and a reflux condenser, and 400 ml of tetrahydrofuran was added thereto and heated and stirred under reflux. 32.5 g of zinc powder which has previously been treated with hydrochloric acid was carefully and gradually added thereto. After the addition, the whole was continuously heated and stirred under reflux for further 30 minutes, and then distilled under reduced pressure. 140 ml of the first fraction was discarded, and all of the remains were distilled-d continuously.

The $^1$H-NMR spectrum (solvent CCl$_4$) of the thus obtained liquid revealed $\delta = 1.8$ ppm (belonging to tetrahydrofuran), $\delta = 3.6$ ppm (belonging to the same) and $\delta = 6.1$ ppm (belonging to the methine of Intermediate (3)). From the NMR integral strength ratio, the content of Intermediate (3) was 20.9 wt %, the yield thereof was 36.6 g, and the yield percentage thereof was 66%.

Synthesis of Intermediate (4)

25.8 g of sodium hydroxide and 150 ml of distilled water were added to a one liter three-neck flask provided with a stirrer and stirred and dissolved. 69.6 g (0.60 mol) of thiophenol was added, stirred and dissolved, and then cooled with ice. The content became separated into two phases and cloudy (i.e., appeared white). While cooling with ice and stirring, 36.6 g (0.30 mol) of Intermediate (3) containing 138.5 g of tetrahydrofuran was dropwise added within 30 minutes. Afterwards, the whole was stirred for an additional 6 hours at room temperature and then was left at room temperature overnight without stirring. The lower layer formed by two layer phase separation was discarded, and the upper layer was transported to a separating funnel, where ethyl acetate was added and the whole was washed with a saturated salt solution, and then dried with Glauber's salt and evaporated under reduced pressure.

The residue was purified by column chromatography with silica gel as a stationary phase and ethyl acetate/n-hexane (=1/100, by volume) as a mobile phase to obtain 77.0 g of Intermediate (4) (an oil). The yield percentage was 95%. The $^1$H-NMR spectrum thereof (solvent: CCl$_4$) revealed $\delta = 7.3$ ppm (belonging to the methine of Intermediate (4)).

Synthesis of Intermediate (5)

77.0 g (0.285 mol) of Intermediate (4) and 173 ml of hydrazine hydrate were added to a 500 ml three-neck flask provided with a stirrer and a reflux condenser and heated and stirred under reflux for 4 hours, whereupon the inner temperature was within the range from 110° to 115° C. The contents, which had been in two phases initially, a uniform phase after the reaction. After keeping the contents over-night without stirring, the contents were transported to a separating funnel, where ethyl acetate was added and the whole was washed with 0.3N sodium hydroxide-containing saturated salt solution, dried with Glauber's salt, and then subjected to column chromatography with silica gel as a stationary phase and methanol/chloroform (=1/5) as a mobile phase for purification.

Thus, 21.1 g (yield percentage: 39%) of Intermediate (5) was obtained in the form of a pale yellow oil. The $^1$H-NMR spectrum (solvent: $(CD_3)_3CO$) revealed $\delta = 3.3$ ppm, $\delta = 5.6$ ppm, $\delta = 5.9$ ppm, and $\delta = 7.2$ ppm.

Synthesis of Intermediate (7)

21.1 g (0.11 mol) of Intermediate (5), 200 ml of methanol and 37.3 g (0.13 mol) of Intermediate (6) obtained in accordance with the method as described in Japanese Patent Application (OPI) No. 171956/84 were added to a 300 ml three-neck flask provided with a stirrer and a reflux condenser and stirred for 4 hours at room temperature. The raw material (5) was confirmed to have disappeared by thin layer chromatography (hereinafter referred to as "TLC").

After confirmation that Intermediate (5) has disappeared, a solution comprising 11.5 g of hydroxylamine hydrochloride and 13.5 g of sodium acetate dissolved in 50 ml of distilled water was added and the mixture was heated and stirred under reflux for 45 minutes. After cooling to room temperature, the insoluble materials were separated off by filtration and the remaining liquid was evaporated under reduced pressure. Ethyl acetate was added to the resultant and dissolved, and the whole was washed with a 0.1N aqueous sodium hydroxide solution, dried with Glauber's salt, and then purified by column chromatography with silica gel as a stationary phase and ethyl acetate/benzene (=1/1) as a mobile phase.

Thus, 30.5 g of Intermediate (7) was obtained in the form of a pale yellow oil. The yield percentage was 66%.

Synthesis of Intermediate (8)

30.5 g (0.072 mol) of Intermediate (7), 50 ml of acetonitrile, 14.1 g of p-toluenesulfonyl chloride and 5.9 ml of pyridine were added to a 300 ml three-neck flask provided with a reflux condenser and a stirrer and stirred for 1 hour at room temperature.

After the raw material, Intermediate (7), was confirmed to have disappeared by TLC, 110 ml of methanol and 5.9 ml of pyridine were added and heated and stirred under reflux for 2 hours. Ethyl acetate was added, the whole was washed with saturated salt solution, and then subjected to column chromatography with silica gel as a stationary phase and ethyl acetate/benzene (=1/1) as a mobile phase. After concentrating the product, n-hexane was added to the resulting product for crystallization. This was filtered and dried, to obtain 6.6 g of Intermediate (8) in the form of a white crystal. The yield percentage was 23% and the m.p.: 224°–226° C. Mass-spectrum parent peak: m/e=403.

Synthesis of Intermediate (9)

6.6 g (16.4 mmol) of Intermediate (8) and 100 ml of ethanol were added to a 300 ml three-neck flask provided with a reflux condenser and a stirrer and formed into a suspension. While heating and stirring under reflux, 0.10 g of $NaWO_4.H_2O$ and 13.5 ml of 35% aqueous hydrogen peroxide solution were added and the mixture was heated and stirred under reflux for 2 hours. After cooling with ice, the crystal that formed were removed by filtration, washed with ethanol, and then dried to obtain 6.0 g of Intermediate (9) in the form of a white crystal. The yield percentage was 84% and the m.p.: 250°–252° C. Mass-spectrum parent peak: m/e=435.

Synthesis of Intermediate (10)

6.0 g (14 mmol) of Intermediate (9) and 100 ml of isopropyl alcohol were added to a 300 ml three-neck flask provided with a reflux condenser and a stirrer, and while heating and stirring under reflux for suspension, 1.0 g of hydrazine hydrate was gradually and dropwise added thereto. Three hours after the dropwise addition, the heating and stirring was continued under reflux. Although the contents were still in the form of a suspension, the completion of the reaction was confirmed by TLC. All the contents were evaporated under reduced pressure, and then dried to solid. It was presumed that 6.6 g of the product obtained comprises 4.2 g of Intermediate (10) and 2.2 g of N,N'-phthalylhydrazine.

Synthesis of Compound No. 1

All of the mixture comprising the above-mentioned Intermediate (10) and N,N'-phthalylhydrazine, 50 ml of N,N-dimethylacetamide and 40 ml of tetrahydrofuran were added to a 200 ml three-neck flask provided with a stirrer and dissolved therein. While stirring this mixture at room temperature, 9.7 g (14 mmol) of Intermediate (11) obtained by a conventional method was added, followed by dropwise addition of a solution of 1.9 ml of triethylamine dissolved in 10 ml of tetrahydrofuran within 10 minutes.

This mixture was stirred for an additional 30 minutes. Although the raw material, Intermediate (11) was confirmed to have disappeared by TLC, the other raw material, Intermediate (10), still remained, and so, 1.9 g of Intermediate (11) and 0.4 ml of triethylamine were further added.

This mixture was stirred for 2 hours at room temperature and then the disappearance of Intermediate (10) was confirmed by TLC. Ethyl acetate was added and the resulting reaction product was washed with a dilute hydrochloric acid-containing saturated salt solution.

After the insoluble material (which was presumed to be N,N'-phthalylhydrazine) was separated by filtration, the resulting liquid was purified by column chromatography with silica gel as a stationary phase and ethyl acetate/chloroform (=1/5) as a mobile phase.

To this purified product was gradually added n-hexane for recrystallization. Thus, 7.7 g of Compound No. 1 was obtained in the form of a white crystal. The yield percentage (based on Intermediate (9)) was 57% and the m.p.: 87°–94° C. Elemental analysis: H 7.48% (theoretical value 7.49%), C 60.58% (theoretical value 60.72%), N 8.60% (theoretical value 8.67%). Mass-spectrum parent peak: m/e=969=[M+H]+.

SYNTHESIS EXAMPLE 2

Synthesis of Compound No. 2

6.6 mmol of compound No. 1 obtained by Synthesis Example 1, 40 ml of methylene dichloride and 0.89 g (6.6 mmol) of N-chloro-succinimide were added to a 50 ml eggplant type flask provided with a stirrer and reacted for 4 hours at room temperature. After keeping the mixture at room temperature overnight without stirring, the mixture was washed with dilute hydrochloric acid and evaporated under reduced pressure.

After purification by column chromatography with silica gel as a stationary phase and chloroform/methanol (=20/1) as a mobile phase, the resulting liquid was evaporated under reduced pressure until a dry solid was obtained, which was dried for an additional 10 hours with a vacuum pump. Thus, 5.2 g (yield percentage: 78%) of compound No. 2 in the form of a non-crystalline white solid was obtained. Elemental analysis: H 7.10% (theoretical value 7.13%), C 58.27% (theoretical value 58.63%), N 8.18% (theoretical value 8.37%). Mass-spectrum parent peak: $m/e = 1003 = [M+H]^+$.

SYNTHESIS EXAMPLE 3

Synthesis of Compound No. 3

Compound No. 3, which was non-crystalline, was obtained from Intermediate (3) of Synthesis Example 1 and trifluoromethanethiol in the same synthesis route as Synthesis Example 1. Elemental analysis: H 6.53% (theoretical value 6.68%), C 53.47% (theoretical value 53.08%), N 8.33% (theoretical value 8.44%), F 5.50% (theoretical value 5.72%), Cl 3.45% (theoretical value 3.56%), S 9.61% (theoretical value 9.66%). Mass-spectrum parent peak: $m/e = 995 = [M+H]^+$.

In order to improve the stability to light or heat of the color image formed by the color image-formation method of the present invention, a known stabilizer can be used. For this purpose, organic compounds capable of improving stability can be used including, for example, hydroquinone derivatives described in U.S. Pat. Nos. 3,935,016 and 3,982,944; hydroquinone-diether derivatives described in U.S. Pat. No. 4,254,216 and Japanese Patent Application (OPI) No. 21004/80; phenol derivatives described in Japanese Patent Application (OPI) No. 145530/79; spiroindane derivatives and methylenedioxybenzene derivatives described in British Patent Application (OPI) Nos. 2,077,455 and 2,062,888 and Japanese Patent Application (OPI) No. 90155/86; chromane derivatives, spirochromane derivatives and coumarane derivatives described in U.S. Pat. Nos. 3,764,337, 3,432,300, 3,574,627 and 3,573,050, Japanese Patent Application (OPI) Nos. 152225/77, 20327/78, 17729/78 and 90156/86; hydroquinone-monoether derivatives and para-aminophenol derivatives described in Japanese Patent Application (OPI) No. 6321/80, British Patent 1,347,556, British Patent Application (OPI) No. 2,066,975 and Japanese Patent Publication No. 12337/79; and bisphenol derivatives described in Japanese Patent Publication No. 31625/73 and U.S. Pat. No. 3,700,455, etc. In particular, spiroindene derivatives, chromane derivatives, spirochromane derivatives, dihydroxybenzene derivatives and dialkoxybenzene derivatives are especially preferred stabilizers.

The use of a metal complex is also effective for improving the stability to light or heat. Such metal complexes are described in U.S. Pat. No. 4,245,018 and Japanese Patent Application (OPI) No. 97353/85, incorporated herein by reference.

Examples of preferred compounds are shown below, but the present invention should not be construed as being limited by these examples.

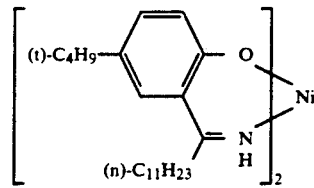

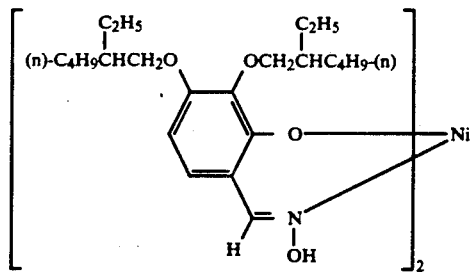

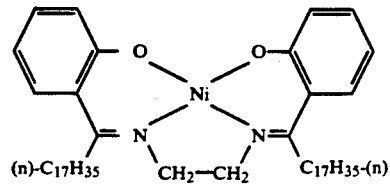

-continued
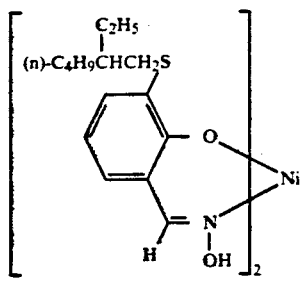 (M-4)
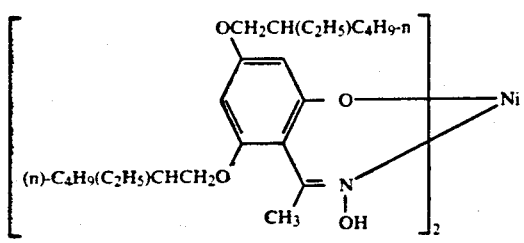 (M-5)
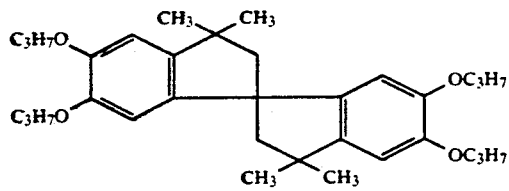 (M-6)
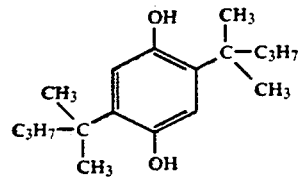 (M-7)
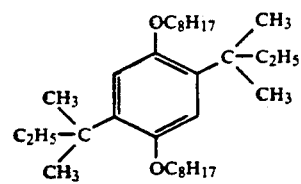 (M-8)
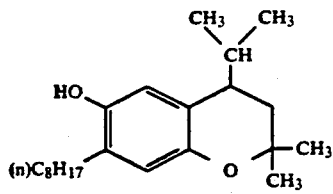 (M-9)
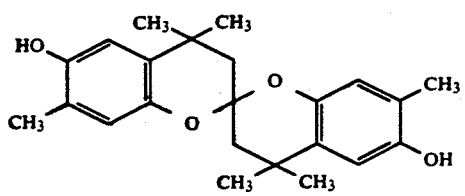 (M-10)

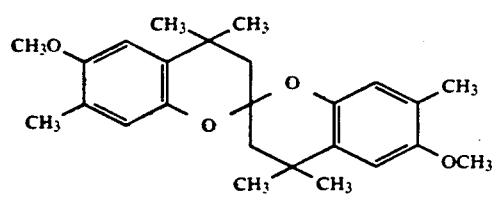  (M-11)
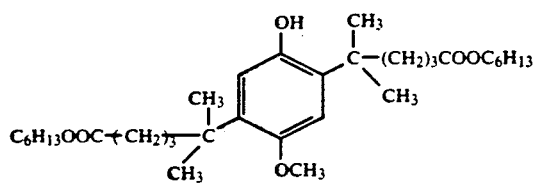  (M-12)
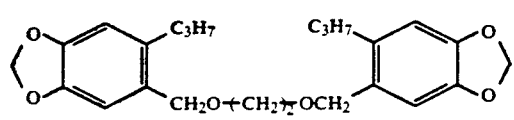  (M-13)
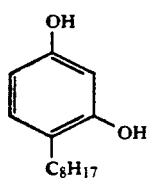  (M-14)
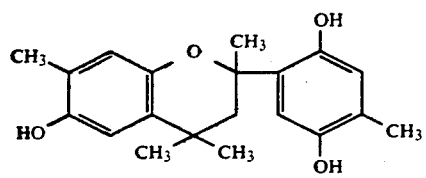  (M-15)
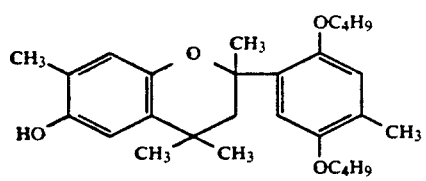  (M-16)
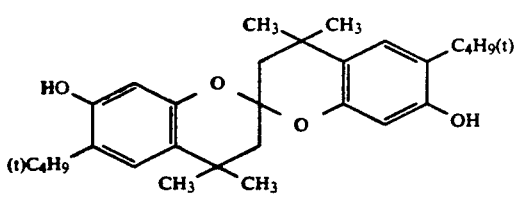  (M-17)
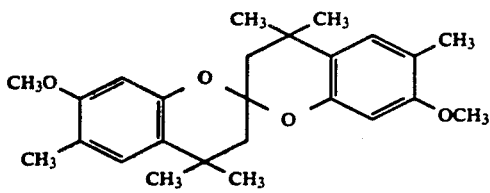  (M-18)
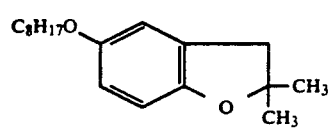  (M-19)

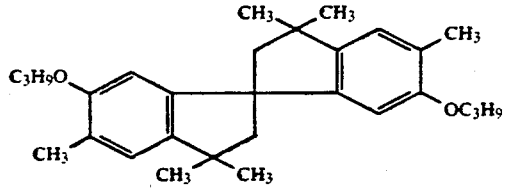
(M-20)

One preferred embodiment of the present invention is a silver halide color photographic material containing the coupler of the present invention.

The coupler of the present invention can be added to the light-sensitive material or can be added to the color developer bath. In the former case, the amount of the coupler to be added to the light-sensitive material is preferably from $1\times10^{-3}$ to 4 mol, more preferably from $5\times10^{-3}$ to 2 mol, per mol of the silver halide in the material; and the coating amount on the silver halide color photographic material support is preferably from $2\times10^{-5}$ to $1\times10^{-2}$ mol/m$^2$, more preferably from $4\times10^{-5}$ to $5\times10^{-3}$ mol/m$^2$. When the coupler is used in the form of a polymer coupler, the amount of the polymer coupler to be added can be so controlled that the coloring part thereof may be the above-mentioned amount. In the latter case where the coupler is added to the developer bath, the amount of the coupler to be added is suitably from 0.0005 to 0.05 mol, preferably from 0.005 to 0.02 mol, per 1000 cc of the bath.

When the coupler of the present invention has a molecular weight of about 250 to 300 or more and has no water-soluble group in order that coupler be non-diffusive, it can be added to the light-sensitive material.

The pyrazoloazole series coupler of the present invention can be introduced into the light-sensitive material by means of various known dispersion methods, for example, by means of typical methods including a solid-dispersion method, an alkali-dispersion method, preferably a latex-dispersion method, and more preferably an oil-in-water dispersion method. In accordance with the oil-in-water dispersion method, the coupler is first dissolved either in a single solution of a high boiling point organic solvent having a boiling point of 175° C. or higher or a so-called assistant solvent having a low boiling point, or in a mixture solution comprising the two, and then the resulting solution is finely dispersed in water or in an aqueous medium such as an aqueous gelatin solution in the presence of a surfactant. Examples of the high boiling point organic solvent are described in U.S. Pat. No. 2,322,027, etc. The dispersion may be accompanied by phase inversion, and the assistant solvent can be removed or reduced by evaporation, noodle washing or ultrafiltration, if desired, prior to coating.

Specific examples of the high boiling point organic solvents include phthalic acid esters (e.g., dibutyl phthalate, dicyclohexyl phthalate, di-2-ethylhexyl phthalate, decyl phthalate, etc.), phosphoric acid or phosphonic acid esters (e.g., triphenyl phosphate, tricresyl phosphate, 2-ethylhexyldiphenyl phosphate, tricyclohexyl phosphate, tri-2-ethylhexyl phosphate, tridecyl phosphate, tributoxyethyl phosphate, trichloropropyl phosphate, di-2-ethylhexylphenyl phosphate, etc.), benzoic acid esters (e.g., 2-ethylhexyl benzoate, dodecyl benzoate, 2-ethylhexyl p-hydroxybenzoate, etc.), amides (e.g., diethyldodecanamide, N-tetradecylpyrrolidone, etc.), alcohols or phenols (e.g., isostearyl alcohol, 2,4-di-tert-amylphenol, etc.), aliphatic carboxylic acid esters (e.g., dioctyl azelate, glycerol tributyrate, isostearyl lactate, trioctyl citrate, etc.), aniline derivatives (e.g., N,N-dibutyl-2-butoxy-5-tert-octylaniline, etc.), hydrocarbons (e.g., paraffin, dodecylbenzene, diisopropylnaphthalene, etc.), etc. As the assistant solvent can be used organic solvents having a boiling point of from about 30° C., preferably from about 50° C., to about 160° C., and specific examples thereof include ethyl acetate, butyl acetate, ethyl propionate, methyl ethyl ketone, cyclohexane, 2-ethoxyethyl acetate, dimethylformamide, etc.

The method and effect of the latex-dispersion method and examples of the latex for impregnation are described, for example, in U.S. Pat. No. 4,199,363, German Patent Application (OLS) Nos. 2,541,274 and 2,541,230, etc.

The silver halide emulsion for use in the present invention may contain any of silver chloride, silver bromide or silver iodide, and especially preferably contains silver chlorobromide which is substantially free from silver iodide.

The expression "substantially free from silver iodide" means that the content of silver iodide in the total silver halide is 3 mol % or less, preferably 1 mol % or less, more preferably 0.5 mol % or less, and most preferably, means that the silver halide does not contain silver iodide.

the incorporation of silver iodide in the emulsion can yield various merits in view of the light-sensitivity thereof in that the light absorption amount is enhanced, adsorption of spectral sensitizing dyes is intensified or desensitization by spectral sensitizing dyes is reduced. However, when rapid development is carried out in the system according to the technique of the present invention, within a short period of time, the retardation of the development speed would cause the retardation of the development speed of all the silver halide grains, which is extremely disadvantageous.

When a minutes amount, for example 1 mol % or less, especially 0.2 mol % or less, of silver iodide is incorporated, the development speed may sometimes be higher than when the silver halide emulsion does not contain any silver iodide. This contradictory result is thought to be due to the fact that incorporation of the silver iodide might cause the formation of a latent image which is stable and which may accelerate development or might cause the formation of a strong latent image, or the iodide ion released during development might act on the grains, which may have a fogged nucleus in the inside thereof by halogen-substituent, thereby to expose the latent images or the fogged nuclei, so that these may be easily developed, or if compound which may inhibit or prevent the development is on the surface of the silver halide grains, the iodide ion might remove the compound, whereby the development speed could, in a relative sense, be accelerated.

Even in such cases, however, it is a matter of course that the silver iodide itself causes the retardation of the development of the silver halide grains containing the same, as opposed to silver chloride or silver bromide. For these reasons, the silver halide emulsions for use in the present invention is preferred to be basically free from silver iodide. However, only in the above-mentioned cases, the incorporation of a slight amount of silver iodide is sometimes advantageous.

When silver chlorobromide is used in the present invention, the halide may have any desired composition ratio and, for example, this may be a pure silver chloride or a pure silver bromide or an intermediate composition between the two. In addition, these compositions may further contain a slight amount of silver iodide as mentioned above.

One preferred composition for use in the present invention is a silver chlorobromide emulsion having a silver bromide content of 10 mol % or more. In order to obtain a chlorobromide emulsion having a sufficient sensitivity without increase of fog, the silver bromide content is preferably 20 mol % or more. However, if rapid processability is required, a chlorobromide emulsion having a silver bromide content of 20 mol % or less, or rather 10 mol % or less, is sometimes preferred.

In particular, if an especially rapid processability is required in the system according to the technique of the present invention, the use of silver chloride is more preferred, which is substantially free from silver bromide to the extent that the content of silver bromide is 3 mol % or less, more preferably 1 mol % or less.

The reduction of the silver bromide content in the emulsion for use in the present invention is preferable not only for the mere improvement in processing speed during development, but also for accelerating the rapid developability of the developer itself, because when the light-sensitive material having such emulsion with a reduced silver bromide content is processed by running processing, the equilibrium amount of the bromide ion as accumulated in the developer, which is determined on the basis of the relation between the ion amount and the replenisher amount, may be of a low concentration.

In order to obtain a light-sensitive material which is hardly fogged and which has a stable color gradation in accordance with the technique of the present invention, the silver bromide content in the emulsion is desired to be higher, and is preferably 50 mol % or more. Especially preferably, the silver bromide content is 65 mol % or more so that an extremely stable emulsion is advantageously obtained. Although an excess content of silver bromide of 95 mol % or more would cause some deterioration of rapid developability, such is not problematic at all, provided that the shape of the crystal grains is varied (for example, to tabular grains, etc.) or some development accelerator (for example, 3-pyrazolidones, thioethers, hydrazines, etc.) is used, and light-sensitive materials which have a high sensitivity and which are stable in storage or processing can be obtained.

The developability of silver halide grains is not determined only by the halogen composition of all the grains but depends upon the halogen distribution in the inside of the grains. Accordingly, the silver halide grains of the emulsion for use in the present invention may have a constitution in the inside of the grains which is different from the overall the halogen composition of the silver halide grains. One typical embodiment of the grains comprises core-shell type or double structure type grains having different halogen compositions between the inside of the grain and the surface layer thereof.

In such grains, the shape of the core and the shape of the complete grain with the shell may be the same or different. For instance, the shape of the core part may be cubic and the shape of the surface part may be octahedral. The complete grain with the shell may be cubic or octahedral.

On the contrary, the core part may be octahedral, and the complete grain with the shall may be cubic or octahedral.

In other cases, the core part may be a definite regular grain, while the complete grain with the shell may be somewhat irregular or amorphous. In addition, the shape may have not only a mere double structure, but also a triple or more multiple structure, or a thin layer of another silver halide having a different composition can be formed on the surface of the core-shell double structure grain.

In order to obtain grains having an internal structure, not only the above-mentioned grains with an enveloped structure may be used, but also so-called contact structure grains can be formed. The contact crystal part may have a different composition from the host crystal and may be joined on to the edge or corner part of the crystal face of the host crystal so as to grow therefrom. Such contact crystal part may be formed on the host crystal part which may either have a uniform halogen composition or have a core-shell type structure. in the grains with such structure, for example, with core-shell structure, the silver bromide content in the core part may be high, while the silver bromide content in the shell part is low or, on the contrary, the silver bromide content in the core part may be low, while that in the shell part is high.

In the same manner, in the grains with contact crystal structure, the silver bromide content in the host crystal may be high, while the silver bromide content in the contact crystal part is relatively low and vice versa.

In the grains with such structure, the boundary between the parts having the different halogen compositions may be either definite or indefinite, a mixed crystal part being formed owing to the composition variation in the latter indefinite boundary; or the boundary may have a positive and continuous structure variation.

In the practice of the present invention, an emulsion containing silver halide grains with some internal structure is preferably used, rather than those with a uniform internal silver halide composition. In particular, grains with such silver halide constitution that the silver bromide content in the surface part of the grain is less than in the inside part thereof are more preferably used.

One typical emulsion for preferable use in the present invention is a core-shell type emulsion containing a higher content of silver bromide in the core part than in the shell part.

Although the molar ratio between the core part and the shell part in the core-shell type grain may be within the range of from 0:100 to 100:0, the ratio (core part/shell part) is preferably selected from the range of from 3/97 to 98/2 in order that the core-shell type grain can definitely be differentiated from a grain with a uniform structure.

When the formation of the shell part is carried out by means of a so-called halogen substitution where the solubility difference between the silver halides on the basis of the kind of respective halogens is utilized and, in particular, when silver chloride is subjected to halogen substitution by the use of a water-soluble bromide, the ratio is preferably more than 98/2, especially preferably more than 99/1. In fact, it is difficult to uniformly coat the surface of the silver halide grains by the halogen substitution, and the shell part is often uniformly formed on the corner part or edge part of the core crystal. The grains thus formed by halogen substitution can be subjected to recrystallization so that the halogen distribution can be made uniform. However, although the thus uniformed grains may have different halogen compositions between the internal part and the surface layer part, it is difficult to specify the core-shell constitutional ratio in the silver halide grain.

When core-shell type silver halide grains are used in the system according to the technique of the present invention, the more preferred ratio of core/shell is between 5/95 and 95/5, more preferably between 7/93 and 90/10, most preferably between 15/85 and 80/20.

The difference in the silver bromide content between the core part and the shell part varies, depending upon the constitutional molar ratio of the core part to the shell part, and the said difference is preferred to be from 3 mol % to 95 mol %, more preferably from 5 mol % to 80 mol %, and most preferably from 10 mol % to 70 mol %. If the difference in the silver bromide content between the core part and the shell part is insufficient, the grains would not be differentiated from grains with a uniform structure; but on the contrary, if the difference is too noticeable, the grains would begin to have problematic properties and, therefore, an insufficient difference or an excess difference is unfavorable. The pertinent composition difference depends upon the constitutional ratio of the core part to the shell part. It is preferred that the composition difference is made large when the constitutional ratio is near to 0/100 or 100/0, while, on the other hand, the composition difference is preferred to be made small when the constitutional ratio is near to 1/1.

The shape of the silver chlorobromide grains for use in the present invention may be cubic or octahedral, as mentioned above, or may additionally be tetradecahedral or rhombic dodecahedral, or may be any other shape. In particular, in the case of contact crystal type grains, although these are not amorphous, contact crystal parts may grow uniformly over the corner and/or edge parts of the host crystal and/or over the faces thereof, to give a regular crystal form. In addition, the grains may be spherical.

In the present invention, octadecahedral grains are preferably used and cubic grains are more preferably used. Further, tabular grains can be used, and in particular, a tabular grain silver halide emulsion wherein tabular silver halide grains having an aspect ratio (which corresponds to the ratio of the diameter of the grain, based upon the corresponding circle, to the thickness thereof) of from 5 to 8 account for 50 mol % or more of the total projection area of the silver halide grains is preferred, as having excellent rapid developability. Particularly, these tabular grains are preferred to have the above-mentioned core/shell type, contact crystal type or the like crystal structure.

The mean size of the grains of the silver halide emulsions for use in the present invention, which is defined as the mean value of the diameter of the corresponding spheres derived from the volume of the respective grains, is preferably from $0.1\mu$ to $2\mu$, especially preferably from $0.15\mu$ to $1.4\mu$.

The grain size distribution may be either narrow or broad and, in particular, monodispersed emulsions are preferred. Especially, monodispersed emulsions comprising regular or tabular grains are preferable in the practice of the present invention. More especially, emulsions where 85% or more, preferably 90% or more, by weight or by number of the total grains have a grain size falling within ±20% of the mean grain size are preferred.

Above all, the use of two or more monodispersed emulsions containing the above-mentioned grains, especially cubic, octahedral or tetradecahedral grains, in combination, or the multiple coating of two or more of such monodispersed emulsions is especially favored as giving an excellent result.

The silver chlorobromide emulsions for use in the present invention can be prepared using the methods described, for example, in P. Glafkides, *Chimie et Physique Photographique* (published by Paul Montel, 1967); G. F. Duffin, *Photographic Emulsion Chemistry* (published by Focal Press, 1966); V. L. Zelikman et al., *Making and Coating Photographic Emulsion* (published by Focal Press, 1964), etc. For example, the silver halide emulsions may be prepared by an acid method, a neutralization method, an ammonia method, etc. Also, a method of reacting a soluble silver salt and soluble halide(s), a single jet method, a double jet method, or a combination thereof may be used. A so-called reverse mixing method capable of forming silver halide grains in the presence of excessive silver ions can be employed.

As one system of the double jet method, a so-called controlled double jet method which keeps the silver ion concentration constant in a liquid phase while forming the silver halide grains can also be employed. A monodispersed silver halide emulsion containing silver halide grains having a regular crystal form with a narrow grain size distribution can be obtained using this method. The above-mentioned grains which can preferably be used in the present invention are desired to be prepared basically in accordance with the double jet method.

The silver halide grains may also be formed or physically ripened in the presence of a cadmium salt, a zinc salt, a lead salt, a thallium salt, an iridium salt or a complex salt thereof, a rhodium salt or a complex salt thereof, an iron salt or a complex salt thereof, etc.

In particular, the iridium salt or the complex salt thereof can be used in an amount of from $10^{-9}$ to $10^{-4}$ mol, more preferably from $10^{-8}$ to $10^{-5}$ mol, per mol of the silver halide. The use of such salt is especially advantageous for obtaining rapid developability and stability even when the silver halide is exposed to illumination which is greater than or less than the normal exposure range.

When physical ripening is carried out in the presence of a known silver halide solvent (for example, ammonia, potassium thiocyanate, or thioethers and thione compounds described in U.S. Pat. No. 3,271,157, Japanese Patent Application (OPI) Nos. 12360/76, 82408/78, 144319/78, 100717/79, 155828/79, etc.), monodispersed silver halide emulsions can be obtained containing grains having a regular crystal shape with a narrow grain size distribution.

For removing soluble salts from the silver halide emulsion after physical ripening, a noodle washing method, a flocculation settling method, an ultrafiltration method, etc., can be used.

The silver halide emulsions for use in the present invention can be chemically sensitized by means of individual sulfur sensitization, selenium sensitization, reduction sensitization or noble metal sensitization or by a combination of those methods.

For example, a sulfur sensitization method using gelatin or a sulfur-containing compound capable of reacting silver (e.g., thiosulfates, thioureas, mercapto compounds, rhodanines, etc.), a reduction sensitization method using a reducing material (e.g., stannous salts, amines, hydrazine derivatives, formamidinesulfinic acid, silane compounds, etc.), a noble metal sensitization method using a metal compound (e.g., gold complex salts and complex salts of metals belonging to group VIII of the Periodic Table, such as platinum, iridium, palladium, rhodium, iron, etc.) can be used individually or as a combination thereof.

For the silver chlorobromide of the present invention, sulfur sensitization or selenium sensitization is preferably used, and it is also preferred to carry out sensitization in the presence of a hydroxyazaindene compound.

For the incorporation of the pyrazoloazole coupler into the silver halide color photographic material for the practical use of the material, the combination of the pyrazoloazole series coupler of the present invention with a silver halide emulsion spectrally sensitized with an oxacarbocyanine dye, an imidacarbocyanine dye and/or an imidaoxacarbocyanine dye is preferred when the coupler is a magenta coupler, and the combination of the coupler of the present invention with a silver halide emulsion spectrally sensitized with a thiacarbocyanine dyes, an oxathiacarbocyanine dye, an oxathiadicarbocyanine dye and/or a thiadicarbocyanine dye is preferred when the coupler is a cyan coupler.

In addition, when the coupler of the present invention is a magenta coupler, it is also preferred to use a thiacarbocyanine dye, an oxathiacarbocyanine dye, an oxathiadicarbocyanine dye and/or a thiadicarbocyanine dye in other layers. Further, it is also preferred to use an oxacarbocyanine dye, an imidacarbocyanine dye and/or an imidaoxacarbocyanine dye in other layers, when the coupler of the present invention is a cyan coupler.

In the case of color photographic materials for prints or reflex color photographic materials, an oxacarbocyanine dye, a thiacarbocyanine dye and a thiadicarbocyanine dye are especially preferred among them.

The emulsions for use in the present invention are generally those which have been physically ripened, chemically ripened and/or spectrally sensitized. Additives which may be used in the ripening or sensitization step are described in *Research Disclosure*, Vol. 176, No. 17643 and Vol. 187, No. 18716, and the relevant parts therein are listed in the Table below.

Conventional photographic additives may also be used in the photographic materials of the present invention, which are also described in the two *Research Disclosures* mentioned above, and the relevant parts therein are also listed in the Table below.

| No. | Kind of Additives | RD 17643 | RD 18716 |
|---|---|---|---|
| 1. | Chemical Sensitizer | p. 23 | p. 648, right column |
| 2. | Sensitivity Enhancer | | p. 648, right column |
| 3. | Spectral Sensitizer and Supersensitizer | pp. 23–24 | from p. 648, right column to p. 649, right column |
| 4. | Brightener | p. 24 | — |
| 5. | Anti-foggant and Stabilizer | pp. 24–25 | p. 649, right column |
| 6. | Light Absorbent, Filter Dye, and UV Absorbent | pp. 25–26 | From p. 649, right column to p. 650, left column |

-continued

| No. | Kind of Additives | RD 17643 | RD 18716 |
|---|---|---|---|
| 7. | Stain-inhibitor | p. 25, right column | p. 650, from left column to right column |
| 8. | Color Image Stabilizer | p. 25 | — |
| 9. | Hardener | p. 26 | p. 651, left column |
| 10. | Binder | p. 26 | p. 651, left column |
| 11. | Plasticizer and Lubricant | p. 27 | p. 650, right column |
| 12. | Coating Assistant and Surfactant | pp. 26–27 | p. 650, right column |
| 13. | Anti-static Agent | p. 27 | p. 650, right column |

Other kinds of color couplers can also be used in the present invention and concrete examples of such couplers are described in patent specifications as referred to in the aforesaid *Research Disclosure* (RD) No. 17643, VII-C through G.

Important dye-forming couplers are those capable of forming the three primary colors (i.e., yellow, magenta and cyan) in a subtractive color process by color-development. Concrete examples of non-diffusive 4-equivalent or 2-equivalent couplers which may be used in the present invention are described in the patent specifications referred to in the aforesaid RD No. 17643, VII-C and D. In addition, other couplers as mentioned below may also preferably be used in the present invention.

As the yellow couplers for use in the present invention, there are ballast group-containing hydrophobic acylacetamide series couplers as typical examples. Specific examples of these couplers are described in U.S. Pat. Nos. 2,407,210, 2,875,057, 3,265,506, etc. In the present invention, 2-equivalent yellow couplers are preferably used and specific examples of these yellow couplers are the oxygen atom-releasing type yellow couplers described in U.S. Pat. Nos. 3,408,194, 3,447,928, 3,933,501, 4,022,620, etc., and the nitrogen atom-releasing type yellow couplers described in Japanese Patent Publication No. 10739/83, U.S. Pat. Nos. 4,401,752, 4,326,024, *Research Disclosure*, No. 18053 (April, 1979), British Patent 1,425,020, West German Patent Application (OLS) Nos. 2,219,917, 2,261,361, 2,329,587, 2,433,812, etc. Among these yellow couplers, α-pivaloylacetanilide couplers are excellent in fastness, particularly with regard to the light fastness of the colored dyes formed, while α-benzoylacetanilide couplers are excellent in coloring density. These couplers are preferred for use in the present invention.

As magenta couplers which can be used in the present invention together with the pyrazoloazole series couplers of the present invention, there are the ballast group-containing hydrophobic indazolone series or cyanoacetyl series couplers, preferably the 5-pyrazolone series couplers and other pyrazoloazole series couplers than the new pyrazoloazole series couplers of the present invention, as typical examples. As the pyrazolone series couplers, those substituted by an arylamino group or an acylamino group at the 3-position thereof are preferred from the viewpoint of the hue and coloring density of the colored dyes formed. Specific examples of these couplers are described in U.S. Pat. Nos. 2,311,082, 2,343,703, 2,600,788, 2,908,573, 3,062,653, 3,152,896, 3,936,015, etc. Also, as the releasable groups for the 2-equivalent 5-pyrazolone series couplers, the nitrogen atom-releasing groups described in U.S. Pat. No. 4,310,619 and the arylthio groups described in U.S.

Pat. No. 4,351,897 are preferred. Furthermore, the 5-pyrazolone series couplers having a ballast group described in European Patent 73,636 give high coloring density.

As the cyan couplers which can be used together with the pyrazoloazole series couplers of the present invention, there are the hydrophobic and non-diffusive naphthol series or phenol series couplers. Specific examples of the naphthol series couplers include the naphthol series couplers described in U.S. Pat. No. 2,474,293 and preferably the oxygen atom-releasing type 2-equivalent naphthol series couplers described in U.S. Pat. Nos. 4,052,212, 4,146,396, 4,228,233 and 4,296,200. Also, specific examples of the phenol series couplers are described in U.S. Pat. Nos. 2,369,929, 2,801,171, 2,772,162, 2,895,826, etc.

Cyan couplers having high fastness to humidity and temperature are preferably used in the present invention and typical examples of these cyan couplers include the phenol series cyan couplers having an alkyl group with 2 or more carbon atoms at the meta-position of the phenol nucleus described in U.S. Pat. No. 3,772,002; the 2,5-diacylamino-substituted phenol series couplers described in U.S. Pat. Nos. 2,772,162, 3,758,308, 4,126,396, 4,334,011, 4,560,635, 4,327,173, West German Patent Application (OLS) No. 3,329,729, European Patent 121,365, etc.; the phenol series couplers having a phenylureido group at the 2-position thereof and an acylamino group at the 5-position thereof described in U.S. Pat. Nos. 3,446,622, 4,333,999, 4,451,559 and 4,427,767; and the condensed ring-containing phenol series couplers described in U.S. Pat. Nos. 4,326,173 and 4,430,423, Japanese Patent Application (OPI) Nos. 164554/84, 159851/85, 102936/83, 134635/83 and 39044/86, and Japanese Patent Application No. 100222/86, etc.

In the present invention, by using couplers which provide colored dyes having the proper diffusibility together with the aforesaid color couplers, the graininess of the color images formed can be improved. Specific examples of the magenta couplers which provide such diffusible dyes are described in U.S. Pat. No. 4,366,237 and British Patent 2,125,570 and specific examples of yellow, magenta and cyan couplers of this type are described in European Patent 96,570 and West German Patent Application (OLS) No. 3,234,533.

The dye-forming couplers and the above-described specific couplers for use in the present invention may form dimers or higher polymers. Typical examples of the polymerized dye-forming couplers are described in U.S. Pat. Nos. 3,451,820 and 4,080,211. Also, specific examples of the polymerized magenta couplers are described in British Patent 2,102,173 and U.S. Pat. No. 4,367,282.

Couplers which may release a photographically useful group in the course of the coupling reaction may also preferably be used in the present invention. DIR-couplers capable of releasing a development inhibitor are described in the patent specifications referred to in the aforesaid RD No. 17643, VII-F, which may advantageously be used in the present invention.

The color photographic material of the present invention may be developed by means of a conventional developing means, as described, for instance, in the aforesaid RD No. 17643, pp. 28-29 and No. 18716, page 651, from the left-hand column to the right-hand column.

The color photographic material of the present invention is in general subjected to a rinsing or stabilization treatment after the development and bleaching-fixation or fixation of the material.

The processing step (or the step for image formation) to be applied to the photographic materials of the present invention is described in detail hereinafter.

In the color development step for the photographic materials of the present invention, the time for development is preferably 5 minutes or less, more preferably 2 minutes and 30 seconds or less, and most preferably from 30 seconds to 2 minutes. The "time for the development" means the time from the first contact of the photographic light-sensitive material being processed with the color developer to the contact of the said material with the processing solution of the next bath, including the time for the transference of the material from the previous bath to the next bath (the so-called "transferring time"). The total processing time from the entrance into the first bath to the way-out from the last bath is preferably 30 minutes or less, more preferably 20 minutes or less, and most preferably 10 minutes or less.

The color developer for use in the development of the photographic materials of the present invention is preferably an alkaline aqueous solution consisting essentially of an aromatic primary amine color developing agent. As the color developing agent, the p-phenylenediamine series compounds are preferably used and specific examples of such compounds include 3-methyl-4-amino-N,N-diethylaniline, 3-methyl-4-amino-N-ethyl-N-$\beta$-hydroxyethylaniline, 3-methyl-4-amino-N-ethyl-N-($\beta$-methanesulfonamidoethyl)aniline, 3-methyl-4-amino-N-ethyl-N-$\beta$-methoxyethylaniline and their sulfates, hydrochlorides, phosphates, p-toluenesulfonates, tetraphenylborates, p-(t-octyl)benzenesulfonates, etc.

Aminophenol series derivatives include, for example, o-aminophenol, p-aminophenol, 4-amino-2-methylphenol, 2-amino-3-methylphenol, 2-hydroxy-3-amino-1,4-dimethylbenzene, etc.

In addition to those agents, the compounds described in L. F. A. Mason, *Photographic Processing Chemistry*, pp. 226-229 (published by Focal Press Co.), U.S. Pat. Nos. 2,193,015 and 2,592,364 and Japanese Patent Application (OPI) No. 64933/73 can also be used. Two or more color developing agents can be used in combination, if desired.

In the practice of the present invention, the temperature during processing with the color developer is preferably from 30° C. to 50° C., and more preferably from 33° C. to 45° C.

As a development accelerator, the color developer may contain benzyl alcohol, but it is preferred that the color developer does not substantially contain benzyl alcohol. The wording "does not substantially contain" means that the color developer may contain benzyl alcohol preferably only in an amount of 2 ml or less, more preferably 0.5 ml or less, per liter of the color developer, and most preferably the color developer does not contain benzyl alcohol.

As other development accelerators, various kinds of compounds can be used. For instance, there may be mentioned various kinds of pyrimidium compounds and other cationic compounds, cationic dyes such as phenosafranine, and neutral salts such as thallium nitrate and potassium nitrate, as typically described in U.S. Pat. No. 2,648,604, Japanese Patent Publication No. 9503/69 and U.S. Pat. No. 3,171,247; nonionic compounds such as polyethylene glycol and derivatives thereof and polythioethers, as described in Japanese Patent Publication No. 9304/69 and U.S. Pat. No. 2,533,990, 2,531,832, 2,950,970 and 2,577,127; thioether series compounds as described in U.S. Pat. No. 3,201,242; and other compounds as described in Japanese Patent Application (OPI) Nos. 156934/83 and 220344/85.

In rapid development, not only the means of accelerating the development, but also the technique of preventing the development fog, is an important factor. As the anti-foggant, alkali metal halides such as potassium bromide, sodium bromide and potassium iodide, as well as organic anti-foggants can, for example, be used. The organic anti-foggants which can be used in the present invention include, for example, nitrogen-containing heterocyclic compounds such as benzotriazole, 6-nitrobenzimidazole, 5-nitroisoindazole, 5-methylbenzotriazole, 5-nitrobenzotriazole, 5-chloro-benzotriazole, 2-thiazolyl-benzimidazole, 2-thiazolylmethyl-benzimidazole and hydroxyazaindolidine; mercapto-substituted heterocyclic compounds such as 1-phenyl-5-mercaptotetrazole, 2-mercaptobenzimidazole and 2-mercaptobenzothiazole; and mercapto-substituted aromatic compounds such as thiosalicylic acid. In particular, halides are especially preferred.

The anti-foggant may be incorporated into the color photographic material in such a manner that it can be dissolved out from the material into the color developer during the processing procedure.

In addition, the color developer may further contain a pH buffer such as alkali metal carbonates, borates and phosphates; a preservative such as hydroxylamine, triethanolamine, the compounds described in West German Patent Application (OLS) No. 2,622,950, sulfites and bisulfites; an organic solvent such as diethylene glycol; a dye-forming coupler, a competing coupler; a nucleating agent such as sodium boron hydride; an auxiliary developing agent such as 1-phenyl-3-pyrazolidone; a tackifier; and a chelating agent such as ethylenediaminetetraacetic acid, nitrilo-triacetic acid, cyclohexanediaminetetraacetic acid, imino-diacetic acid, N-hydroxymethylethylenediamine-triacetic acid, diethylenetriamine-pentaacetic acid, triethylenetetramine-hexaacetic acid, as well as amino-polycarboxylic acids, such as the compounds typically described in Japanese Patent Application (OPI) No. 195845/83, 1-hydroxyethylidene-1,1'-diphosphonic acid, the organic phosphonic acids described in *Research Disclosure*, No. 18170 (May, 1979), amino-phosphonic acids including aminotris(methylene phosphonic acid) and ethylenediamine-N,N,N',N'-tetramethylene-phosphonic acid, and the phosphonocarboxylic acids described in Japanese Patent Application (OPI) Nos. 102726/77, 42730/78, 121127/79, 4024/80, 4025/80, 126241/80, 65955/80 and 65956/80 and *Research Disclosure*, No. 18170 (May, 1979), etc.

The color development bath system can be divided into two or more, if desired, so that a color developer replenisher may be replenished from the first bath or from the last bath, whereby development time can be shortened or the amount of the replenisher to be used can be reduced.

After color development, the silver halide color photographic material thus processed is generally bleached. The bleaching treatment can be carried out simultaneously with the fixation treatment (bleach-fixation), or can be carried out separately.

As the bleaching agent, compounds of polyvalent metals such as iron (III), cobalt (III), chromium (VI), copper (II), etc., as well as peracids, quinones, nitroso compounds, can, for example, be used. For instance, ferricyanides, bichromates, and organic complexes with iron (III) or cobalt (III), for example, complexes of an aminopolycarboxylic acid such as ethylenediamine-tetraacetic acid, diethylenetriamine-pentaacetic acid, nitrilo-triacetic acid or 1,3-diamino-2-propanoltetraacetic acid, or complexes with an organic acid such as citric acid, tartaric acid or malic acid; persulfates and manganates; nitrosophenol, etc., can be used. In particular, potassium ferricyanide, sodium ethylenediamine-tetraacetate/iron (III), ammonium ethylenediamine-tetraacetate/iron (III), ammonium triethylenetetramine-pentaacetate/iron (III) and persulfates are especially useful among them. Ethylenediamine-tetraacetic acid/iron (III) complexes can be used both in an independent bleaching solution and in a combined bleaching and fixing solution.

Various kinds of accelerators can be incorporated into the bleaching solution or the bleach-fixing solution, if desired. For example, bromide ion and iodide ion, as well as the thiourea series compounds described in U.S. Pat. No. 3,706,561, Japanese Patent Publication Nos. 8506/70 and 26586/74 and Japanese Patent Application (OPI) Nos. 32735/78, 36233/78 and 37016/78, the thiol series compounds described in Japanese Patent Application (OPI) Nos. 124424/78, 95631/78, 57831/78, 32736/78, 65732/78 and 5 52534/79 and U.S. Pat. No. 3,893,858, the heterocyclic compounds described in Japanese Patent Application (OPI) Nos. 59644/74, 140129/75, 28426/78, 141623/78, 104232/78 and 35727/79, the thioether series compounds described in Japanese Patent Application (OPI) Nos. 20832/77, 25064/80 and 26506/80, the quaternary amines described in Japanese Patent Application (OPI) No. 84440/73, and the thiocarbamoyls or the like compounds described in Japanese Patent Application (OPI) No. 42349/74, etc. can be used.

As the fixing agent, there may be mentioned thiosulfates, thiocyanates, thioether series compounds, thioureas and a large amount of iodides, and thiosulfates which are generally used as fixing agents. As the preservative for the bleach-fixing solution or fixing solution, sulfites and bisulfites as well as carbonyl-bisulfite adducts are preferred.

After the bleach-fixation or fixation treatment, the photographic materials thus processed are generally rinsed with water. In the rinsing step, various kinds of known compounds can be incorporated into the rinsing bath for the purpose of prevention of precipitation or of economization of water. For example, a water softener for prevention of precipitation, such as inorganic phosphoric acids, aminopolycarboxylic acids and organic phosphoric acids; a bactericide or fungicide for prevention of propagation of various kinds of bacteria, algae or fungi; a hardener such as magnesium salts or aluminium salts; as well as a surfactant for prevention of drying load or unevenness can be added to the rinsing bath, if desired. In addition, the compounds described in L. E. West, *Phot. Sci. and Eng.*, Vol. 9, No. 6 (1965), etc. can also be used. In particular, the addition of a chelating agent or fungicide is effective.

The rinsing step is generally carried out in a countercurrent system using two or more rinsing tanks, so as to economize the amount of water to be used. A stabilization treatment can be carried out in place of the rinsing step, and the multi-stage countercurrent stabilization system described in Japanese Patent Application (OPI) No. 8543/82 is typical. In this stabilization step, two to nine countercurrent tanks are necessary. Various kinds of compounds are added to the stabilization baths so as to stabilize the image formed. For instance, various kinds of buffers so as to adjust the film pH (e.g., within the pH range of from 3 to 8), for example, comprising a combination of borates, metaborates, borax, phosphates, carbonates, potassium hydroxide, sodium hydroxide, aqueous ammonia, monocarboxylic acids, dicarboxylic acids, polycarboxylic acids, etc., as well as formalin, etc. are typical. In addition, a water softener (such as inorganic phosphoric acids, amino-polycarboxylic acids, organic phosphoric acids, amino-polyphosphoric acids, phosphonocarboxylic acids, etc.), a fungicide (such as benzoisothiazolinone, isothiazolone, 4-thiazolinebenzimidazole, halogenated phenols, etc.), a surfactant, a brightening agent, a hardener or other various kinds of additives can be used, if desired. In the use of these additives, two or more kinds of compounds having the same or different functions can be used together.

As the film pH-adjusting agent for the photographic materials after processed, an ammonium salt is preferably added to the processing bath, and various kinds of ammonium salts including ammonium chloride, ammonium nitrate, ammonium sulfate, ammonium phosphate, ammonium sulfite and ammonium thiosulfate can be used for this purpose.

The present invention can be applied to various kinds of color photographic materials. As typical examples, there may be mentioned color negative films for general movie use, color reversal films for slides or television, as well as color papers, color positive films and color reversal papers, etc. In these materials, a transmission-type support or reflection-type support is used.

The "reflection-type support" means a support capable of intensifying the reflectivity of the material so as to strengthen the sharpness of the color image formed in the silver halide emulsion layer of the material. The reflection-type support of this kind includes a support base coated with a hydrophobic resin containing a dispersion of a light-reflective substance such as titanium oxide, zinc oxide, calcium carbonate or calcium sulfate, and a support made of a hydrophobic resin containing a dispersion of the light reflective substance. For instance, there may be mentioned baryta papers, polyethylene-coated papers, polypropylene series synthetic papers and transparent supports which have a reflective layer thereon or which contain a reflective substance therein, including, for example, a glass paper, polyester films such as polyethylene terephthalate, cellulose triacetate or cellulose nitrate, polyamide films, polycarbonate films, polystyrene film, etc. The support can be selected adequately in accordance with the use and the object of the photographic materials.

The following examples are intended to illustrate the present invention but not to limit it in any way. Unless otherwise specified, all parts, percents and ratios are by weight.

EXAMPLE 1

Production of dye for formation of image in silver halide color photographic material and determination of visible absorption spectrum and molecular extinction coefficient

Production of Dye 2.5 g (2.6 mmol) of the aforesaid Compound No. 1 of the present invention, 65 ml of chloroform and 50 ml of distilled water were put in a 300 ml three-neck flask provided with a stirrer and, while stirred, 3.75 g of sodium carbonate, 0.81 g of 4-amino-3-methyl-N-ethyl-N-($\beta$-methyl-sulfonamidoethyl)aniline monosulfate and 1.65 g of ammonium persulfate were added thereto in the named order. The reaction product became colored blue to bluish green.

After continuously stirring for 1 hour at room temperature, the upper layer (aqueous layer) was removed and the remaining layer was washed well with a diluted aqueous hydrochloric acid solution and then purified by column chromatography using silica gel as a stationary phase and methanol/chloroform (=1/100, by volume) as a mobile phase and thereafter re-purified by column chromatography using ethyl acetate/chloroform (=2/5) as a mobile phase. After evaporation under reduced pressure to dryness, the resulting solid was further dried by the action of a vacuum pump for 10 hours to finally obtain 2.4 g of an amorphous image-forming dye (D-1) having the following structural formula. Yield: 75%.

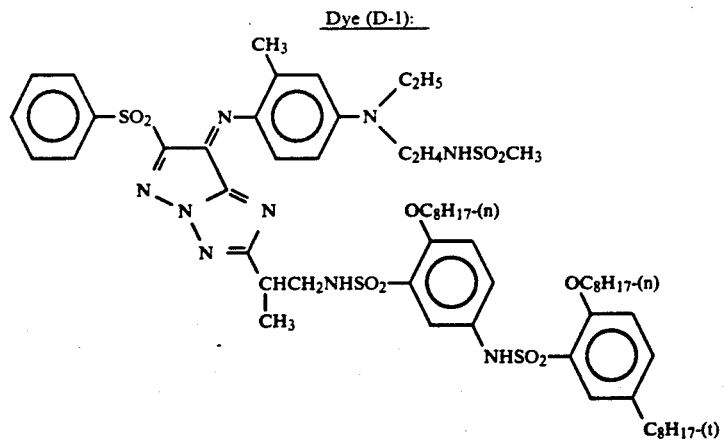

Dye (D-1):

Elementary Analysis: Measured: H 7.35%, C 59.24%, N 10.19%. Theoretical: H 7.25%, C 59.04%, N 10.13%.

Mass Spectrum, Main Peak: m/e=1235=[M+H]$^+$

In the same manner, a comparative dye (D-2) was formed from a comparative coupler (C-2), which is described in U.S. Pat. No. 4,540,654 and has the following structural formula.

Comparative Coupler (C-2):

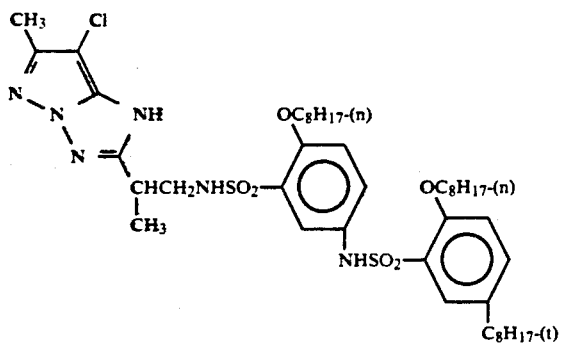

Comparative Dye (D-2):

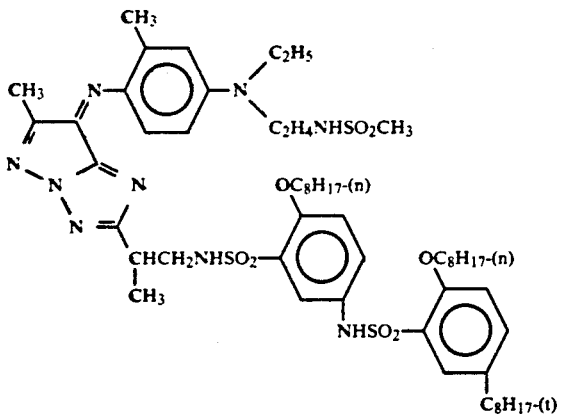

Comparison of Dyes with Respect to Visible Absorption Spectrum 2.00 mg of each of the image forming Dye (D-1) of the present invention and the comparative Dye (D-2) was individually put in a 100 ml volumetric flask, and after ethyl acetate (special grade chemical reagent) was added thereto to dissolve at room temperature, the ethyl acetate was further added up to the indicator. The whole was gently shaken to make uniform, and then this was put in a quartz cell with 1 cm thickness and the visible absorption spectrum of the dye was measured by the use of an ultraviolet and visible spectrophotometer by Shimazu Seisakusho Ltd. (Japan). The visible absorption spectra of both dyes are shown in FIG. 1, in which the maximum absorption value was standardized to be 1 (one) in both cases. In FIG. 1, the solid line shows the visible absorption spectrum of the Dye (D-1) of the present invention and the dashed line shows that of the comparative Dye (D-2).

As is apparent from FIG. 1, the Dye (D-1) of the present invention gave a more sharp absorption spectrum than the comparative Dye (D-2), and therefore it is understood that the hue of the former would be more sharp than that of the latter. In addition, it is noted that the maximum absorption wavelength from the Dye (D-1) of the present invention is much longer than that of the comparative Dye (D-2). The comparative Dye (D-2) color is magenta while the Dye (D-1) of the present invention is cyan.

Comparison of Dyes with Respect to Molecular Extinction Coefficient

The molecular extinction coefficient of each of the Dye (D-1) of the present invention and the comparative Dye (D-2) was calculated from the respective maximum absorption value and the molar density. This is shown in Table 1 below.

TABLE 1

|  | Molecular Weight | Amount Used (mg) | Molar Concentration (mol/liter) | Maximum Absorption Strength | Molecular Extinction Coefficient ($mol^{-1} \cdot liter \cdot cm^{-1}$) |
| --- | --- | --- | --- | --- | --- |
| Dye of the Invention (D-1) | 1236.71 | 2.00 | $1.62 \times 10^{-5}$ | 1.438 | $8.89 \times 10^4$ |
| Comparative Dye (D-2) | 1110.56 | 2.00 | $1.81 \times 10^{-5}$ | 1.005 | $5.58 \times 10^4$ |

Table 1 shows that the Dye (D-1) of the present invention has a much higher molecular extinction coefficient than the comparative Dye (D-2). Accordingly, a smaller amount of the coupler Compound No. 1 of the present invention can provide the intended photographic density.

The above results indicate that the introduction of an especially strong electron-attractive group into the pyrazoloazole series coupler as its substituent causes a noticeable shift in the maximum absorption wavelength of the image-forming dye formed from the coupler to a deep color with an intensification of the sharpness of the absorption of the dye to provide a sharp color and a substantial increase in the molecular extinction coefficient of the dye. (In fact, the benzenesulfonyl substituent group (for $R_1$) of Compound No. 1 of the present invention has a Hammett's substituent constant $\sigma_p$ of 0.70, while the methyl substituent group (for $R_1$) of the Comparative coupler (C-2) has a constant $\sigma_p$ of $-0.17$.)

EXAMPLE 2

Comparison between Dye (D-1) of the present invention and comparative cyan dyes from known cyan couplers with respect to the visible absorption spectrum and the molecular extinction coefficient In the same manner as Example 1, comparative image-forming cyan dyes (indoaniline dyes) (D-3) and (D-4) were formed from the following cyan coupler (C-3) which is described in U.S. Pat. No. 3,772,002 and the following cyan coupler (C-4) which is described in U.S. Pat. No 4,560,635.

Comparative Coupler (C-3):

-continued the Dye (D-1) is shorter than that of the comparative Dyes (D-3) and (D-4).

TABLE 2

|  | Molecular Weight | Amount Used (mg) | Molar Concentration (mol/liter) | Maximum Absorption Strength | Molecular Extinction Coefficient (mol$^{-1}$ · liter · cm$^1$) |
|---|---|---|---|---|---|
| Dye of the Invention (D-1) | 1236.71 | 2.00 | $1.62 \times 10^{-5}$ | 1.438 | $8.89 \times 10^4$ |
| Comparative Dye (D-3) | 741.42 | 2.00 | $2.70 \times 10^{-5}$ | 0.661 | $2.45 \times 10^4$ |
| Comparative Dye (D-4) | 852.91 | 2.00 | $2.34 \times 10^{-5}$ | 0.551 | $2.35 \times 10^4$ |

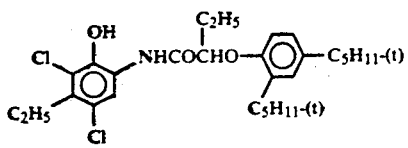

Comparative Coupler (C-4):

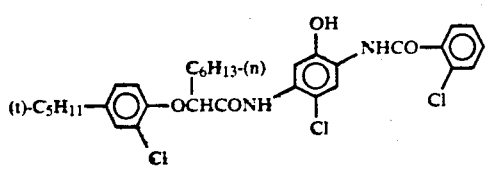

Comparative Dye (D-3):

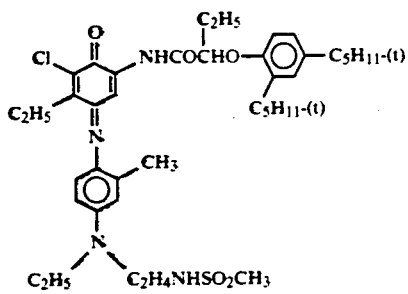

Comparative Dye (D-4)

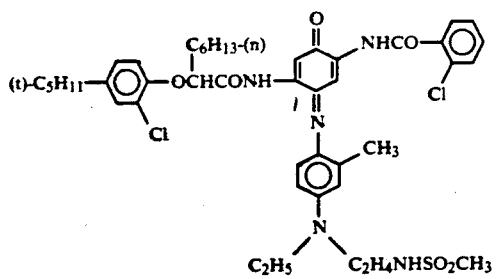

Figure 2:
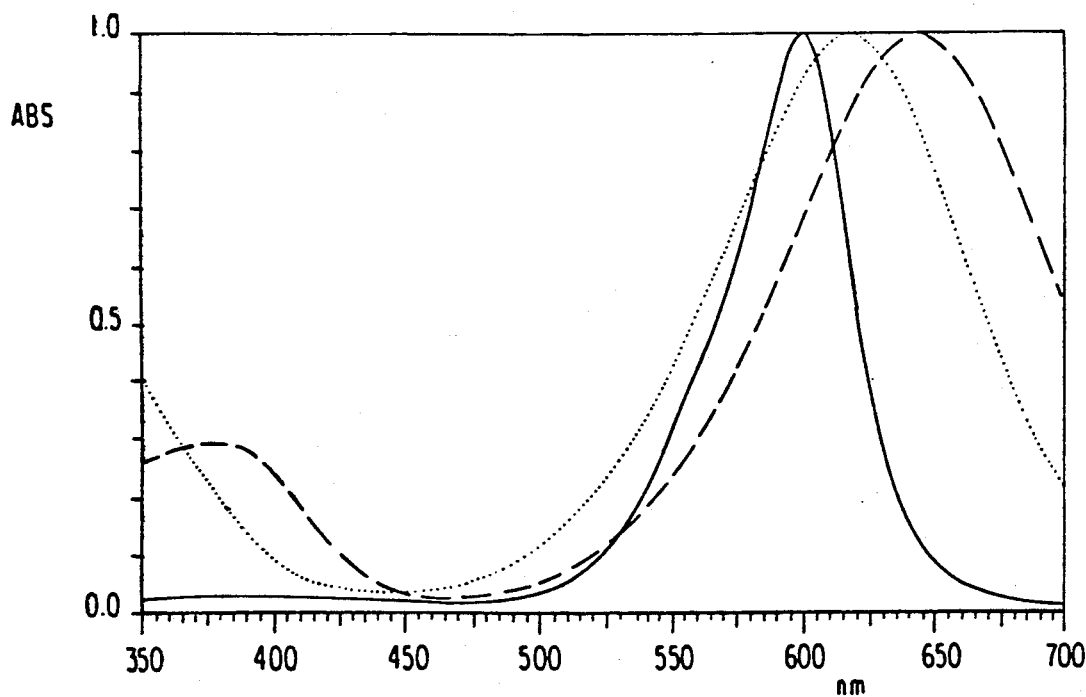
In FIG. 2, the solid line shows the visible absorption spectrum of the image forming cyan dye (D-1) formed from the pyrazoloazole series cyan coupler compound No. 1 of the present invention in the silver halide color photographic material of Example 2. The dashed line shows the visible absorption spectrum of the cyan dye formed from the comparative phenol series cyan coupler (C-3) in the material of Example 1, and the dotted line shows a visible absorption spectrum of the cyan dye formed from the comparative phenol series cyan coupler (C-4) in the material of Example 2.

In the same manner as Example 1, the visible absorption spectrum and the molecular extinction coefficient of each dye were measured and these were compared with those of the Dye (D-1) of the present invention. FIG. 2 shows the comparison of the visible absorption spectra of the dyes. The absorption spectrum of the Dye (D-1) of the present invention is much more sharp than those of the comparative Dyes (D-3) and (D-4) and, in addition, the former has almost no absorption in the blue light range of from 400 to 500 nm. Accordingly, the hue of the Dye (D-1) was an extremely sharp cyan color, although the maximum absorption wavelength of Table 2 shows that the Dye (D-1) of the present invention provides a much higher molecular extinction coefficient than the comparative Dye (D-3) and Dye (D-4).

The above results indicate that the image-forming cyan dye formed from the cyan coupler of the present invention provides a much sharper absorption spectrum than the image-forming cyan dyes formed from the conventional phenol series cyan couplers and, therefore, the former can provide a sharper cyan tone with a molecular extinction coefficient which is much higher than that of the latter. Accordingly, an extremely small amount of the coupler of the present invention can provide the intended photographic density.

EXAMPLE 3

A solution formed by heating at 50° C. 0.016 mol of the pyrazoloazole series coupler Compound No. 1 or 13 or the comparative pyrazoloazole series magenta coupler C-2 used in the previous Example 1 or the comparative phenol series cyan coupler (C-3) or (C-4) used in the previous Example 2, 10 g of tricresyl phosphate and 40 ml of ethyl acetate was emulsified and dispersed in 80 g of a gelatin solution containing 0.8 g of sodium dodecylbenzenesulfonate and 8 g of gelatin.

Next, the emulsified dispersion thus obtained was blended with 145 g of a red-sensitive silver chlorobromide emulsion (Cl/Br=50/50, mol %) (containing 7 g of Ag), and 10 ml of 2% sodium 2-hydroxy-4,6-dichloro-s-triazine was added thereto as a hardener. The resulting emulsion was coated on a paper support laminated with polyethylene on both surfaces. The coupler was coated at a rate of 0.6 mmol/m$^2$. A gelatin-protective layer was superposed over this layer (in an amount of 1 g/m$^2$ gelatin), to obtain a monochromic silver halide photographic material. The thus formed samples were designated as Sample Nos. 1 to 5.

The same process as in the preparation of Sample No. 1 was repeated, except that 0.016 mol of a coupler (C-5) shown below was further added in addition to 0.016 mol of Compound No. 1 of the present invention, whereby Sample No. 6 was prepared.

Coupler (C-5):

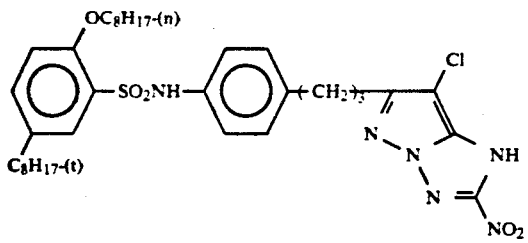

Each sample was exposed through a continuous wedge for sensitometry and then processed as follows:

| Color Development Procedure (33° C.): | |
|---|---|
| 1. Color Development | 3 min 30 sec |
| 2. Bleach-fixation | 1 min 30 sec |
| 3. Rinsing with Water | 2 min 30 sec |

The processing solution used in each processing step was as follows:

| Color Developer: | |
|---|---|
| Benzyl Alcohol | 15.0 ml |
| Diethylene Glycol | 8.0 ml |
| Ethylenediamine-tetraacetic Acid | 5.0 g |
| Sodium Sulfite | 2.0 g |
| Anhydrous Potassium Carbonate | 30 g |
| Hydroxylamine Sulfate | 3.0 g |
| Potassium Bromide | 0.6 g |
| 4-Amino-N-ethyl-N-($\beta$-methanesulfonamido-ethyl)-m-toluidine Sesquisulfate Monohydrate | 5.0 g |
| Water to make | 1 liter |
| | (pH 10.2) |
| Bleach-Fixing Solution | |
| Ethylenediamine-tetraacetic Acid | 4.0 g |
| Ferric Ethylenediamine-tetraacetate | 40 g |
| Sodium Sulfite | 5.0 g |
| Sodium Thiosulfate (70 wt % aq. soln.) | 150 ml |
| Water to make | 1 liter |

Each sample was dried and then the absorption spectrum of each sample was measured by the use of an ultraviolet and visible spectrophotometer provided with an integrating sphere (by Shimazu Seisakusho, Ltd., Japan).

In addition, the sharpness of the absorption peak was evaluated on the basis of the half peak width value as graded in accordance with the following five ranks (A) through (E), the peak width value being the peak width between the two points of the wavelength (nm) having an absorbance of one second the absorbance of the maximum absorption peak.

| Rank | Half Peak Width |
|---|---|
| A | Less than 75 nm |
| B | From 75 nm to less than 90 nm |
| C | From 90 nm to less than 105 nm |
| D | From 105 nm to less than 120 nm |
| E | More than 120 nm |

The results obtained are given in Table 3 below.

TABLE 3

| Sample No. | Coupler | Color Hue | Sharpness of Absorption Peak |
|---|---|---|---|
| 1 | Compound No. 1 | Cyan | A |
| 2 | Compound No. 13 | Bluish purple | B |
| 3 | Comparative magenta coupler (C-2) | Magenta | C |
| 4 | Comparative cyan coupler (C-3) | Cyan | E |
| 5 | Comparative cyan coupler (C-4) | Cyan | E |
| 6 | Compound No. 1 and Coupler (C-5) | Blue to Cyan | C |

From the above results, it is noted that the silver halide photographic material samples formed by coating the pyrazoloazole series cyan or magenta coupler of the present invention can form a color image exhibiting a sharp absorption spectrum and, in turn, sharp color.

EXAMPLE 4

The same process as in Example 3 was repeated, except that Sample Nos. 1 and 6 were subjected to color development using the following color developer which was prepared within one hour.

| Color Developer: | |
|---|---|
| Benzyl Alcohol | 40.0 ml |
| Diethylene Glycol | 8.0 ml |
| Ethylenediamine-tetraacetic Acid | 5.0 g |
| Anhydrous Potassium Carbonate | 30 g |
| Potassium Bromide | 0.6 g |
| 4-Amino-N-ethyl-N-($\beta$-methanesulfonamido-ethyl)-m-toluidine Sesquisulfate Monohydrate | 10.0 g |
| Deaerated water (by bubbling with helium gas for one hour) to make | 1 liter |

It was found that the silver halide photographic material samples formed by coating the pyrazoloazole series cyan or magenta coupler of the present invention formed a color image exhibiting a sharp absorption spectrum and sharp color.

EXAMPLE 5

A multilayer color photographic paper (A) was prepared by forming the layers having the compositions shown below on a paper support coated on both surfaces with polyethylene. The coating compositions for the layers were prepared as follows.

Coating Compositions for First Layer 27.2 ml of ethyl acetate and 7.7 ml of solvent (Solv-1) were added to and dissolved in 10.65 g of yellow coupler (ExY1), 8.11 g of yellow coupler (ExY2) and 4.4 g of color image stabilizer (Cpd-1), and the resulting solution was emulsified and dispersed in 185 ml of 10% aqueous gelatin solution containing 8 ml of 10% sodium dodecylbenzenesulfonate. On the other hand, the blue-sensitive sensitizing dye as shown below was added to a monodispersed cubic silver chlorobromide emulsion (silver bromide: 80.0 mol %) having a mean grain size of 0.81 $\mu$m and a variation coefficient of 0.11 in an amount of $5 \times 10^{-4}$ mol per mol of the silver. The previously prepared emulsion dispersion and the silver halide emulsion were blended and dissolved to obtain a coating solution for the first layer comprising the composition as shown below.

In the same manner as the preparation of the first layer coating solution, the other coating solutions for the second to seventh layers were prepared. As the gelatin hardening agent in each layer, sodium 1-hydroxy-3,5-di-chloro-s-triazine was used.

The following compounds were used as the spectral-sensitizing dye in each emulsion layer.

Blue-sensitive Emulsion Layer:

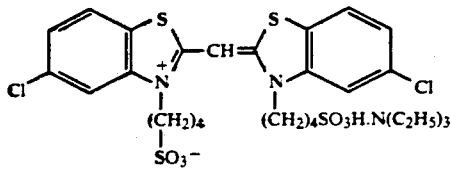

(5.0 × 10$^{-4}$ mol per mol of silver halide)

Green-sensitive Emulsion Layer:

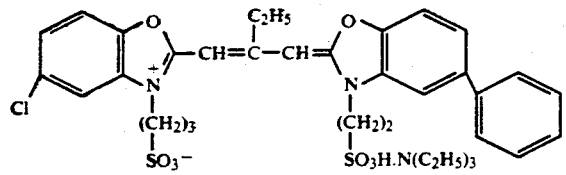

(4.0 × 10$^{-4}$ mol per mol of silver halide)

and

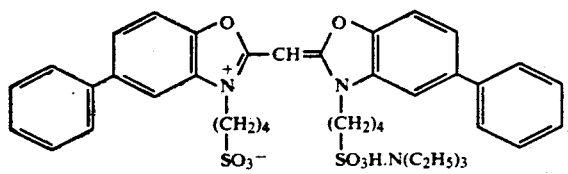

(7.0 × 10$^{-5}$ mol per mol of silver halide)

Red-sensitive Emulsion Layer:

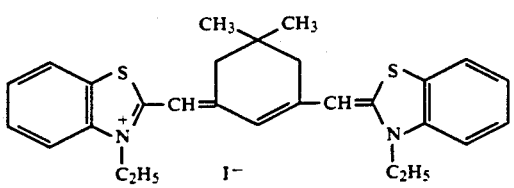

(0.9 × 10$^{-4}$ mol per mol of silver halide)

To the red-sensitive emulsion layer was added the following compound in an amount of 2.6 × 10$^{-3}$ mol per mol of the silver halide.

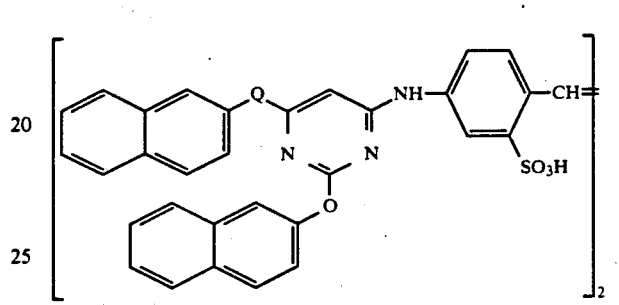

To each of the blue-sensitive emulsion layer, green-sensitive emulsion layer and red-sensitive emulsion layer was added 1-(5-methylureidophenyl)-5-mercaptotetrazole in an amount of 4.0 × 10$^{-6}$ mol, 3.0 × 10$^{-5}$ mol, and 1.0 × 10 mol, respectively, per mol of the silver halide.

To each of the blue-sensitive emulsion layer and green-sensitive emulsion layer was added 4-hydroxy-6-methyl-1,3,3a,7-tetrazaindene in an amount of 1.2 × 10$^{-2}$ mol, and 1.1 × 10$^{-2}$ mol, respectively, per mol of the silver halide.

For anti-irradiation, the following dyes were added:

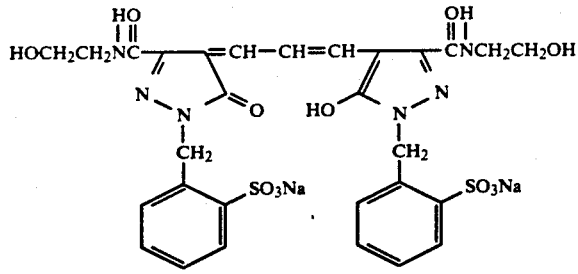

and

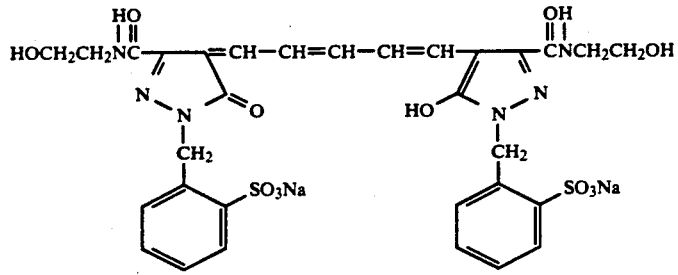

Layer Constitution

The composition of each layer is shown below. In the following layer composition, the numbers along the right hand margin indicate the amount of the ingredient coated (g/m²). The amount of silver halide is represented by the amount of silver coated.

Support

Polyethylene-laminated paper (containing white pigment (TiO₂) and a bluish dye ultramarine) in the polyethylene on the side of the first layer).

| First Layer: Blue sensitive layer | |
|---|---|
| Silver Halide Emulsion (Br: 80 mol %; mean grain size: 1.1 μm; variation coefficient 0.10, cubic grains) | 0.26 |
| Gelatin | 1.83 |
| Yellow Coupler (ExY1) | 0.46 |
| Yellow Coupler (ExY2) | 0.35 |
| Color Image Stabilizer (Cpd-1) | 0.19 |
| Solvent (Solv-1) | 0.35 |
| Second Layer: Color Mixing Preventing Layer | |
| Gelatin | 0.99 |
| Color Mixing Preventing Agent (Cpd-2) | 0.08 |
| Third Layer: Green-sensitive Layer | |
| Silver Halide Emulsion (Br: 80 mol %; mean grain size: 0.43 μm; variation coefficient 0.10, cubic grains) | 0.16 |
| Gelatin | 1.79 |
| Magenta Coupler (ExM1) | 0.32 |
| Color Image Stabilizer (Cpd-3) | 0.20 |
| Color Image Stabilizer (Cpd-4) | 0.05 |
| Solvent (Solv-2) | 0.65 |
| Fourth Layer: Ultraviolet Absorbing Layer | |
| Gelatin | 1.58 |
| Ultraviolet Absorbent (UV-1) | 0.62 |
| Color Mixing Preventing Agent (Cpd-5) | 0.05 |
| Solvent (Solv-3) | 0.24 |
| Fifth Layer: Red-sensitive Layer | |
| Silver Halide Emulsion (Br: 70 mol %; mean grain size: 0.55 μm; variation coefficient 0.13, cubic grains) | 0.23 |
| Gelatin | 1.34 |
| Cyan Coupler (ExC) | 0.24 |
| Color Image Stabilizer (Cpd-6) | 0.17 |
| Polymer (Cpd-7) | 0.30 |
| Solvent (Solv-4) | 0.23 |
| Sixth Layer: Ultraviolet Absorbing Layer | |
| Gelatin | 0.53 |
| Ultraviolet Absorbent (UV-1) | 0.21 |
| Solvent (Solv-3) | 0.08 |
| Seventh Layer: Protective Layer | |
| Gelatin | 1.33 |
| Acrylic-modified copolymer of polyvinyl alcohol (modification degree of 17%) | 0.17 |
| Liquid parafin | 0.03 |

The following compounds were used in preparation of the multilayer color photographic paper (A).

(ExY1)

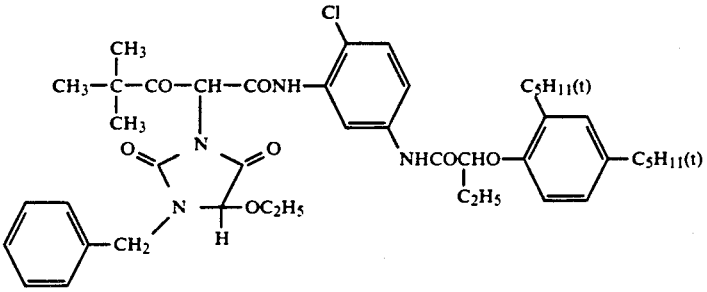

(ExY2)

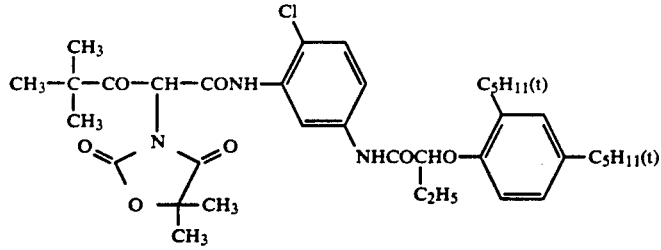

(ExM1)

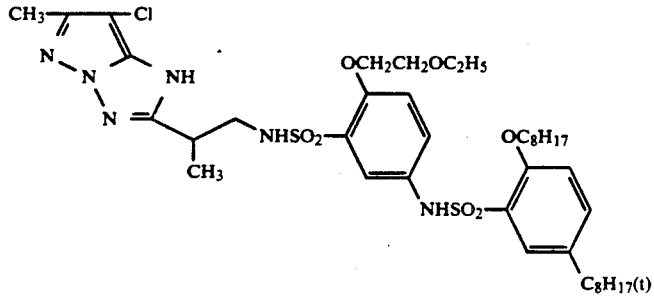

(ExC)

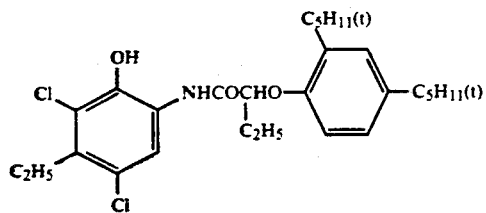
(Cpd-1)
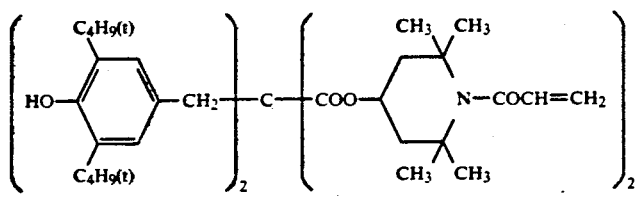
(Cpd-2)
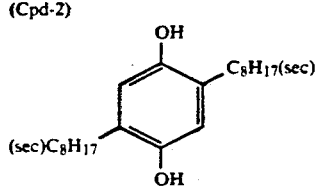
(Cpd-3)
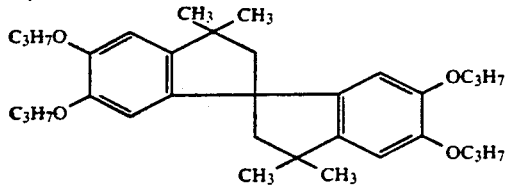
(Cpd-4)
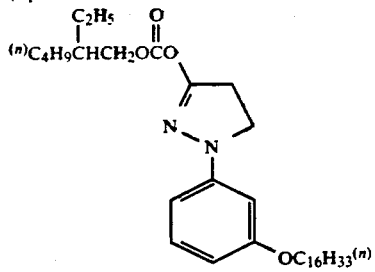
(Cpd-5)
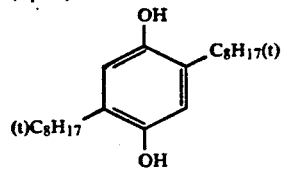
(Cpd-6)
a 5/8/9 (by weight) mixture of the compounds
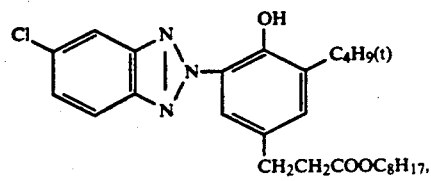

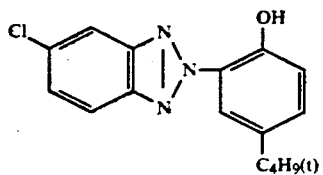
and
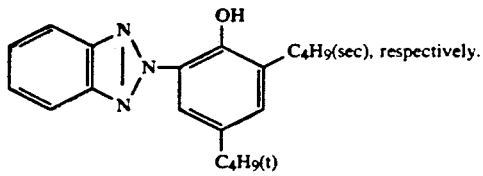
C₄H₉(sec), respectively.
(Cpd-7)
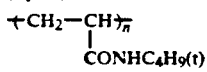
(mean molecular weight: 50,000)
(UV-1)
a 2/9/8 (by weight) mixture of the compounds
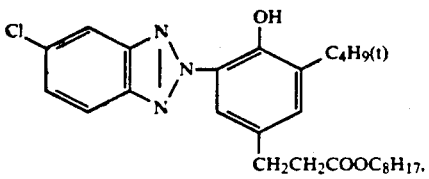
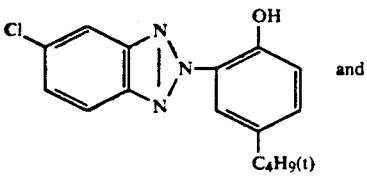
and
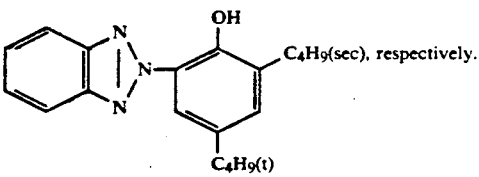
C₄H₉(sec), respectively.
(Solv-1)
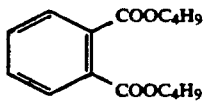
(Solv-2)
a 2/1 (by volume) mixture of the compounds
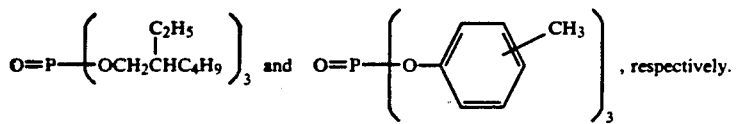
, respectively.
(Solv-3)
(Solv-4)

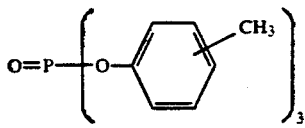

In the same manner as the preparation of the photographic paper (A), another photographic paper (B) was prepared in which the equivalent molar amount of Compound No. 1 of the present invention was used in place of the cyan coupler (ExC) in the fifth layer.

Each of these photographic papers (A) and (B) thus prepared was exposed to sensitometric gradation through each of blue, green and red filters using a sensitometer (FWH-type by Fuji Photo Film Co., light source color temperature: 3200° K.). The exposure was effected for 1/10 second to provide an exposure of 250 CMS.

After exposure, each of papers (A) and (B) was subjected to process (A) comprising the steps of color development, bleach-fixation and rinsing. The temperature and the time in each step are mentioned below.

| Step | Process (A): Temperature | Time |
| --- | --- | --- |
| Color Development | 33° C. | 3 min 30 sec |
| Bleach-fixation | 33° C. | 1 min 30 sec |
| Rinsing with water | 24 to 34° C. | 3 min |
| Drying | 70 to 80° C. | 1 min |

The processing solution used in each step had the following composition.

| Color Developer: | |
| --- | --- |
| Water | 800 ml |
| Diethylenetriamine-pentaacetic Acid | 1.0 g |
| Nitrilo-triacetic Acid | 1.5 g |
| Benzyl Alcohol | 15 ml |
| Diethylene Glycol | 10 ml |
| Sodium Sulfite | 2.0 g |
| Potassium Bromide | 0.5 g |
| Potassium Carbonate | 30 g |
| N-ethyl-N-(β-methanesulfonamido-ethyl)-3-methyl-4-aminoaniline Sulfate | 5.0 g |
| Hydroxylamine Sulfate | 4.0 g |
| Brightening Agent (WHITEX 4B, by Sumitomo Chemical Co., Japan) | 1.0 g |
| Water to make | 1000 ml |
| pH (25° C.) | 10.20 |
| Bleach-Fixing Solution: | |
| Water | 400 ml |
| Ammonium Thiosulfate (70 wt % aq. soln) | 150 ml |
| Sodium Sulfite | 18 g |
| Ammonium Ethylenediamine-tetraacetate/iron (III) | 55 g |
| Disodium Ethylenediamine-tetraacetate | 5 g |
| Water to make | 1000 ml |
| pH (25° C.) | 6.70 |

The samples thus obtained by processing photographic papers (A) and (B) by the above-mentioned procedure (A) were designated as Sample Nos. 7 and 8.

On the other hand, after photographic papers (A) and (B) were exposed to the same gradation as mentioned above, these were subjected to process (B) comprising the steps of color development, bleach-fixation and rinsing as mentioned below. The samples thus obtained by processing photographic papers (A) and (B) by procedure (B) below were designated as Sample Nos. 9 and 10. The temperature and the time in each step of process (B) are mentioned below.

| Step | Process (B): Temperature | Time |
| --- | --- | --- |
| Color Development | 38° C. | 1 min 40 sec |
| Bleach-fixation | 30 to 34° C. | 1 min |
| Rinsing (1) | 30 to 34° C. | 20 sec |
| Rinsing (2) | 30 to 34° C. | 20 sec |
| Rinsing (3) | 30 to 34° C. | 20 sec |
| Drying | 70 to 80° C. | 50 sec |

Rinsing was carried out using a three tank countercurrent system from rinsing bath (3) to rinsing bath (1).

The processing solution used in each step had the following composition.

| Color Developer: | |
| --- | --- |
| Water | 800 ml |
| Diethylenetriamine-pentaacetic Acid | 1.0 g |
| 1-Hydroxyethylidene-1,1-diphosphonic Acid (60 wt %) | 2.0 g |
| Nitrilo-triacetic Acid | 2.0 g |
| 1,3-Diamino-2-propanol | 4.0 g |
| 1,4-Diazabicyclo[2,2,2]octane | 6.0 g |
| Potassium Bromide | 0.5 g |
| Potassium Carbonate | 30 g |
| N-ethyl-N-(β-methanesulfonamido-ethyl)-3-methyl-4-aminoaniline Sulfate | 5.5 g |
| Diethylhydroxylamine | 4.0 g |
| Brightening Agent (UVITEX CK, by Ciba-Geigy) | 1.5 g |
| Water to make | 1000 ml |
| pH (25° C.) | 10.25 |
| Bleach-Fixing Solution: | |
| Water | 400 ml |
| Ammonium Thiosulfate (70 wt % aq. soln) | 200 ml |
| Sodium Sulfite | 20 g |
| Ammonium Ethylenediamine-tetraacetate/iron (III) | 60 g |
| Disodium Ethylenediamine-tetraacetate | 10 g |
| Water to make | 1000 ml |
| pH (25° C.) | 7.00 |
| Rinsing Solution: | |
| Ion Exchanged Water (Each of Ca-content Mg-content was 3 ppm or less.) | |

Next, in the same manner as the preparation of photographic papers (A) and (B), other photographic papers (C) and (D) were prepared except that each emulsion layer was replaced by the cubic silver chlorobromide emulsion set forth below, which contained silver bromide in an amount of from 0.4 to 1 mol % and the spectral-sensitizing dye used in each of the blue-sensitive layer, green-sensitive layer and red-sensitive layer was replaced by the compound set forth below.

Cubic Silver Chlorobromide Emulsions:

-continued

|  | Mean Grain Size (μm) | Coefficient | Silver Bromide Content (mol %) |
|---|---|---|---|
| Blue-sensitive Layer | 0.97 | 0.13 | 0.7 |
| Green-sensitive Layer | 0.39 | 0.12 | 0.4 |
| Red-sensitive Layer | 0.48 | 0.09 | 1.0 |

Blue-sensitive Emulsion Layer:

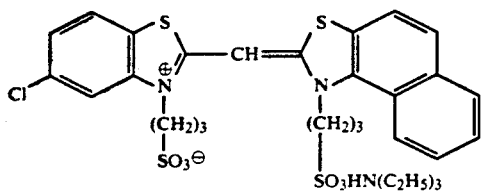

($7 \times 10^{-4}$ mol per mol of silver halide)

Green-sensitive Emulsion Layer:

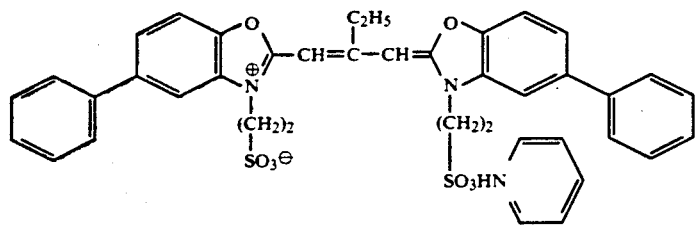

($4 \times 10^{-4}$ mol per mol of silver halide)

Red-sensitive Emulsion Layer:

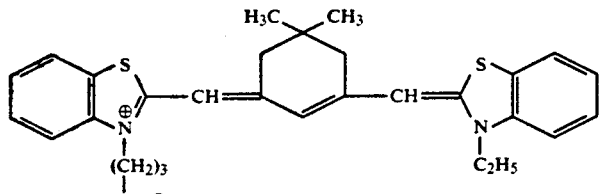

($0.9 \times 10^{-4}$ mol per mol of silver halide)

Photographic papers (C) and (D) were exposed to the same gradation as the above-mentioned Sample Nos. 7 to 10 and then subjected to process (C) comprising the steps of color development, bleach-fixation and stabilization as mentioned below. The samples obtained by processing photographic papers (C) and (D) by process (C) were designated as Sample Nos. 11 and 12. The temperature and the time of process (C) are shown below.

| Process (C): | | |
|---|---|---|
| Step | Temperature | Time |
| Color Development | 35° C. | 45 sec |
| Bleach-fixation | 30 to 36° C. | 45 sec |
| Stabilization (1) | 30 to 37° C. | 20 sec |
| Stabilization (2) | 30 to 37° C. | 20 sec |
| Stabilization (3) | 30 to 37° C. | 20 sec |
| Stabilization (4) | 30 to 37° C. | 30 sec |
| Drying | 70 to 85° C. | 60 sec |

The stabilization was carried out using a four tank countercurrent system from stabilization bath (4) to stabilization bath (1).

The processing solution used in each step had the following composition.

| Color Developer: | |
|---|---|
| Water | 800 ml |
| Ethylenediamine-tetraacetic Acid | 2.0 g |
| Triethanolamine | 8.0 g |
| Sodium Chloride | 1.4 g |
| Potassium Carbonate | 25 g |
| N-ethyl-N-(β-methanesulfonamido-ethyl)-3-methyl-4-aminoaniline Sulfate | 5.0 g |
| N,N-diethylhydroxylamine | 4.2 g |
| 5,6-Dihydroxybenzene-1,2,4-trisulfonic Acid | 0.3 g |
| Brightening Agent (4,4'-Diaminostilbene Series Compound) | 2.0 g |
| Water to make | 1000 ml |
| pH (25° C.) | 10.10 |
| Bleach-Fixing Solution: | |
| Water | 400 ml |
| Ammonium Thiosulfate (70 wt % aq. soln) | 100 ml |
| Sodium Sulfite | 18 g |
| Ammonium Ethylenediamine-tetraacetate/iron (III) | 55 g |
| Disodium Ethylenediamine-tetraacetate | 3 g |
| Glacial Acetic Acid | 8 g |
| Water to make | 1000 ml |

| -continued | |
|---|---|
| pH (25° C.) | 5.5 |
| Stabilizer Solution: | |
| Formaldehyde (37 wt % aq. soln) | 0.1 g |
| Formaldehyde/Sulfurous Acid Adduct | 0.7 g |
| 5-Chloro-2-methyl-4-isothiazolin-3-one | 0.02 g |
| 2-Methyl-4-isothiazolin-3-one | 0.01 g |
| Copper Sulfate | 0.005 g |
| Water to make | 1000 ml |
| pH (25° C.) | 4.0 |

In each of comparative sample Nos. 7, 9 and 11 and Sample Nos. 8, 10 and 12 of the present invention thus processed, the spectral absorption of the part of the sample exposed through the red filter and developed (i.e., the cyan-colored part) was measured. An ultraviolet and visible spectrophotometer by Shimazu Seisakusho Ltd. (Japan) was used to measure the absorption spectrum.

The results obtained by these measurements show that the samples of the present invention gave a sharper color with almost no side absorption in comparison to the comparative samples. Thus, the effect of the present invention was also shown with multilayer color photographic papers, as well as with the monochromic papers in the previous examples.

Furthermore, the samples of the present invention were shown to have a higher extinction coefficient than the comparative samples. Therefore, the couplers of the present invention can provide a color density which is higher than that of the comparative couplers when used in the same dye amount.

In the process of the preparation of the color coupler (ExM1) in the third layer was replaced with (ExM2) shown below to form color photographic papers (E) to (H), respectively, and the magenta coupler was replaced by (ExM3) shown below to form color photographic papers (I) to (L), respectively. These papers were processed in the same manner as above and the same results were obtained.

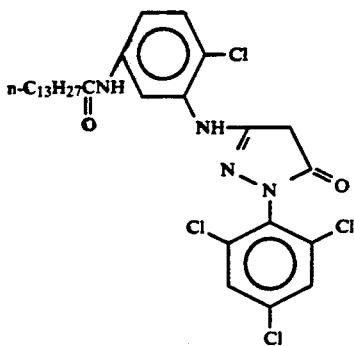
(ExM2)

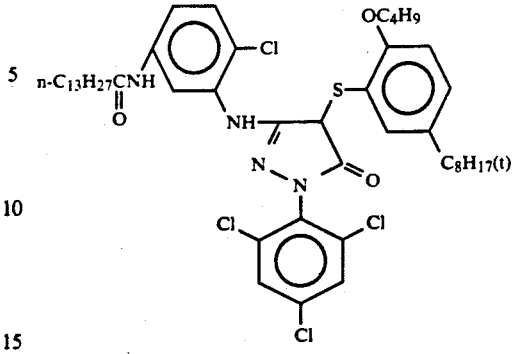
(ExM3)

EXAMPLE 6

A color reversal photographic material was prepared by forming the first to twelfth layers as mentioned below on a paper support, both surfaces of which were coated with polyethylene. The polyethylene coated on the side of the first layer contained titanium white as a white pigment and a slight amount of ultramarine as a bluish dye.

Layer Constitution

The composition of each layer is shown below. In the following layer composition, the numbers along the right hand margin indicate the amount of ingredient coated ($g/m^2$). The amount of silver halide is represented by the amount of silver coated.

| First Layer: Gelatin Layer | |
|---|---|
| Gelatin | 1.30 |
| Second Layer: Anti-halation Layer | |
| Black Colloidal Silver | 0.10 |
| Gelatin | 0.70 |
| Third Layer: Low Sensitivity Red-sensitive Layer | |
| Silver Chloroiodobromide EM1 spectrally-sensitized with red-sensitive dye (ExS-1, 2 and 3; 1/1/1 by mol) (silver chloride 1 mol %, silver iodide 4 mol %, mean grain size: 0.3 μm, grain size distribution: 10%, iodine-in-core type core/shell cubic grains) | 0.06 |
| Silver iodobromide EM2 spectrally-sensitized with red-sensitive dye (ExS-1, 2 and 3; 1/1/1 by mol) (silver iodide 5 mol %, mean grain size: 0.45 μm, grain size distribution: 20%, tabular grains with an aspect ratio of 5) | 0.10 |
| Gelatin | 1.00 |
| Cyan Coupler (ExC-1) | 0.14 |
| Cyan Coupler (Compound No. 1 of the Invention) | 0.07 |
| Anti-fading Agent (Cpd-8, 9, 10 and 15, each in an equimolar amount) | 0.12 |
| Coupler Dispersing Agent (Cpd-11) | 0.03 |
| Coupler Solvent (Solv-5, 6 and 7, each in an equimolar amount) | 0.06 |
| Fourth Layer: High Sensitivity Red-Sensitive Layer | |
| Silver Iodobromide EM3 spectrally-sensitized with red-sensitive dye (ExS-1, 2 and 3; 1/1/1 by mol) (silver iodide: 6 mol %, mean grain size: 0.75 μm, grain size distribution: 25%, iodine-in-core type tabular grains with an aspect ratio of 8) | 0.15 |
| Gelatin | 1.00 |
| Cyan Coupler (ExC-1) | 0.20 |
| Cyan Coupler (Compound No. 1 of the Invention) | 0.10 |
| Anti-fading Agent (Cpd-8, 9, 10 and 15, each in an equimolar amount) | 0.15 |

| -continued | |
|---|---|
| Coupler Dispersing Agent (Cpd-11) | 0.03 |
| Coupler Solvent (Solv-5, 6 and 7, each in an equimolar amount) | 0.10 |
| Fifth Layer: Interlayer | |
| Magenta Colloidal Silver | 0.02 |
| Gelatin | 1.00 |
| Color Mixing Preventing Agent (Cpd-12 and 13, each in an equimolar amount) | 0.08 |
| Color Mixing Preventing Agent Solvent (Solv-8 and 9, each in an equimolar amount) | 0.16 |
| Polymer Latex (Cpd-14) | 0.10 |
| Sixth Layer: Low Sensitivity Green-sensitive Layer | |
| Silver Chloroiodobromide EM4 spectrally-sensitized with green-sensitive dye (ExS-4) (silver chloride: 1 mol %, silver iodide: 2.5 mol %, mean grain size: 0.28 μm, grain size distribution: 12%, iodine-in-core type core/shell cubic grains) | 0.04 |
| Silver Iodobromide EM5 spectrally-sensitized with green-sensitive dye (ExS-4) (silver iodide: 2.8 mol %, mean grain size: 0.45 μm, grain size distribution: 12%, tabular grains with an aspect ratio of 5) | 0.06 |
| Gelatin | 0.80 |
| Magenta Coupler (ExM-1) | 0.10 |
| Anti-fading Agent (Cpd-15) | 0.10 |
| Stain-inhibitor (Cpd-16) | 0.01 |
| Stain-inhibitor (Cpd-17) | 0.001 |
| Stain-inhibitor (Cpd-18) | 0.01 |
| Coupler Dispersing Agent (Cpd-11) | 0.05 |
| Coupler Solvent (Solv-8 and 10, each in an equimolar amount) | 0.15 |
| Seventh Layer: High Sensitivity Green-Sensitive Layer | |
| Silver Iodobromide EM6 spectrally-sensitized with green-sensitive dye (ExS-4) (silver iodide: 3.5 mol %, mean grain size: 0.9 μm, grain size distribution: 23%, uniform iodine-type tabular grains with an aspect ratio of 9) | 0.10 |
| Gelatin | 0.80 |
| Magenta Coupler (ExM-1) | 0.10 |
| Anti-fading Agent (Cpd-15) | 0.10 |
| Stain-inhibitor (Cpd-16) | 0.01 |
| Stain-inhibitor (Cpd-17) | 0.001 |
| Stain-inhibitor (Cpd-18) | 0.01 |
| Coupler Dispersing Agent (Cpd-11) | 0.05 |
| Coupler Solvent (Solv-8 and 10, each in an equimolar amount | 0.15 |
| Eighth Layer: Yellow Filter Layer | |
| Yellow Colloidal Silver | 0.20 |
| Gelatin | 1.00 |
| Color Mixing Preventing Agent (Cpd-13) | 0.06 |
| Color Mixing Preventing Agent Solvent (Solv-8 and 9, each in an equimolar amount) | 0.15 |
| Polymer Latex (Cpd-14) | 0.10 |
| Ninth Layer: Low Sensitivity Blue-sensitive Layer | |
| Silver Chloroiodobromide EM7 spectrally-sensitized with blue-sensitive dye (ExS-5 and 6; 1/1 by mol) | 0.07 |

| -continued | |
|---|---|
| (silver chloride: 2 mol %, silver iodide: 2.5 mol %, mean grain size: 0.35 μm, grain size distribution: 8%, iodine-in-core type core/shell cubic grains) | |
| Silver Iodobromide EM8 spectrally-sensitized with bluen-sensitive dye (ExS-5 and 6; 1/1 by mol) (silver iodide: 2.5 mol %, mean grain size: 0.45 μm, grain size distribution: 16%, tabular grains with an aspect ratio of 6) | 0.10 |
| Gelatin | 0.50 |
| Yellow Coupler (ExY-1) | 0.20 |
| Stain-inhibitor (Cpd-17) | 0.001 |
| Stain-inhibitor (Cpd-12) | 0.10 |
| Coupler Dispersing Agent (Cpd-11) | 0.05 |
| Coupler Solvent (Solv-6) | 0.05 |
| Tenth Layer: High Sensitivity Blue-Sensitive Layer | |
| Silver Iodobromide EM9 spectrally-sensitized with blue-sensitive dye (ExS-5 and 6; 1/1 by mol) (silver iodide: 2.5 mol %, mean grain size: 1.2 μm, grain size distribution: 21%, tabular grains with an aspect ratio of 14) | 0.25 |
| Gelatin | 1.00 |
| Yellow Coupler (ExY-1) | 0.40 |
| Stain-inhibitor (Cpd-17) | 0.002 |
| Anti-fading Agent (Cpd-12) | 0.10 |
| Coupler Dispersing Agent (Cpd-11) | 0.05 |
| Coupler Solvent (Solv-6) | 0.10 |
| Eleventh Layer: Ultraviolet Absorbing Layer | |
| Gelatin | 1.50 |
| Ultraviolet Absorbent (Cpd-9, 19 and 28, each in an equimolar amount) | 1.00 |
| Color Mixing Preventing Agent (Cpd-12 and 20, each in an equimolar amount) | 0.06 |
| Dispersing Agent (Cpd-11) | 0.05 |
| Ultraviolet Absorbent Solvent (Solv-5 and 6, each in an equimolar amount) | 0.15 |
| Anti-irradiation Dye (Cpd-21 and 22, each in an equimolar amount) | 0.02 |
| Anti-irradiation Dye (Cpd-23 and 24, each in an equimolar amount) | 0.02 |
| Twelfth Layer: Protective Layer | |
| Fine Silver Chlorobromide Grains (silver chloride: 97 mol %, mean grain size: 0.2 μm) | 0.07 |
| Modified Poval | 0.02 |
| Gelatin | 1.50 |
| Gelatin Hardener (H-1) | 0.17 |

In each layer, Alkanol XC (by Dupont) and sodium alkylbenzenesulfonate were used as an emulsification and dispersion assistant and succinate and Magafac F-120 (by Dianippon Ink Co., Japan) were used as a coating assistant. In the silver halide- or colloidal silver-containing layer, a stabilizer (Cpd-25, 26 and 27, each in an equimolar amount) was used. The compounds used in the present invention are shown below.

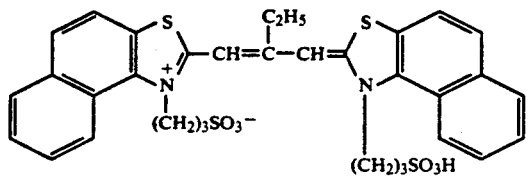

ExS-1

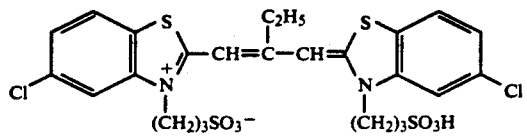

ExS-2

ExS-3

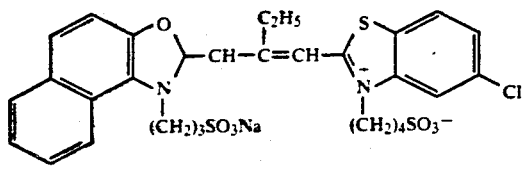
ExS-4
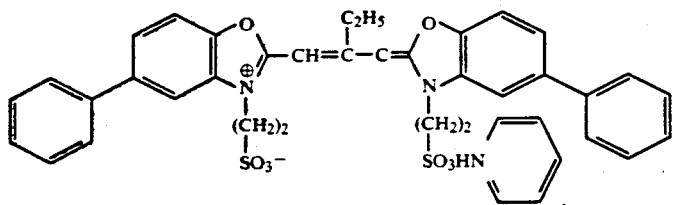
ExS-5
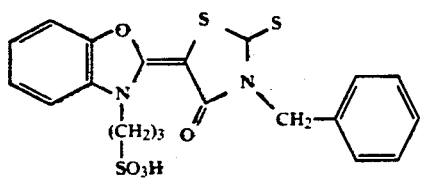
ExS-6
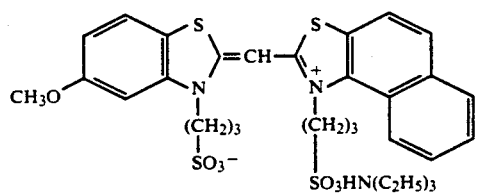
Cpd-8
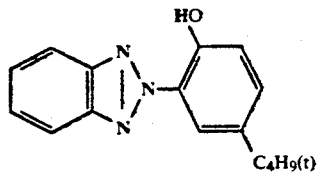
Cpd-9
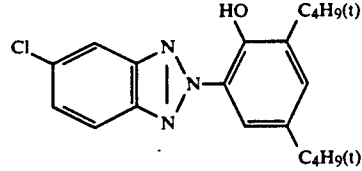
Cpd-10
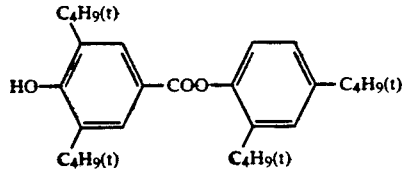
Cpd-11
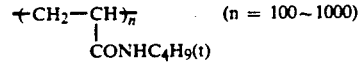
$(n = 100 \sim 1000)$
Cpd-12
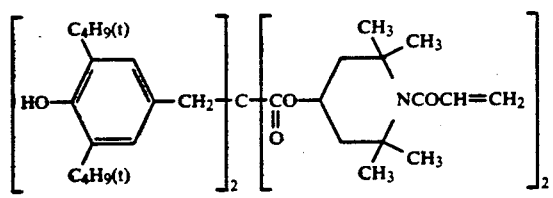
Cpd-13
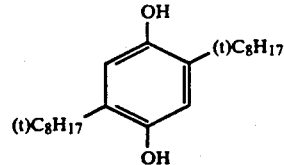
Cpd-14
Polyethyl Acrylate
Cpd-15
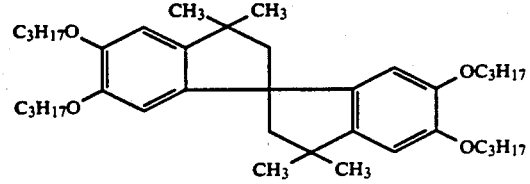
Cpd-16
Cpd-17

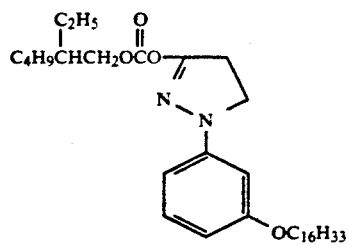
Cpd-18
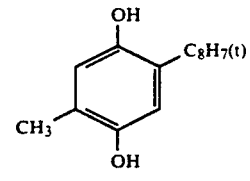
Cpd-19
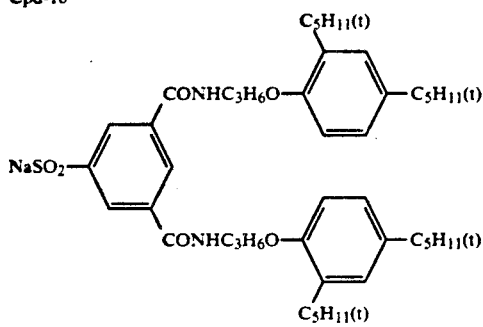
Cpd-20
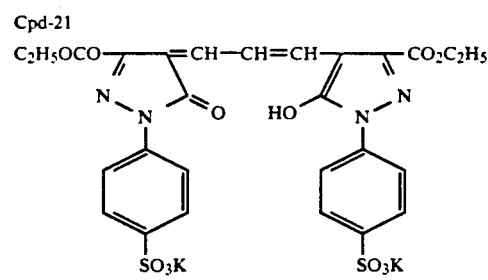
Cpd-21
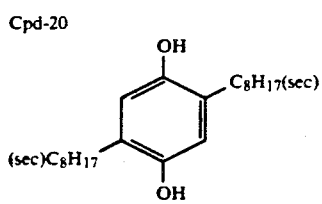
Cpd-22
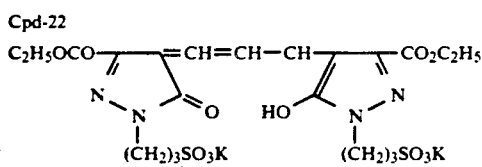
Cpd-23
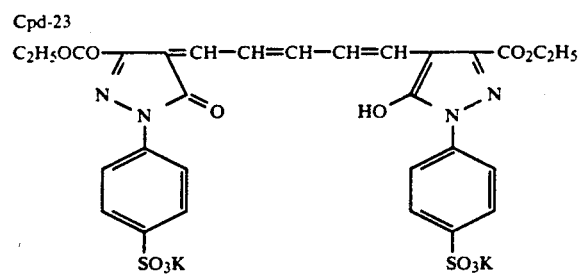
Cpd-24
Cpd-25
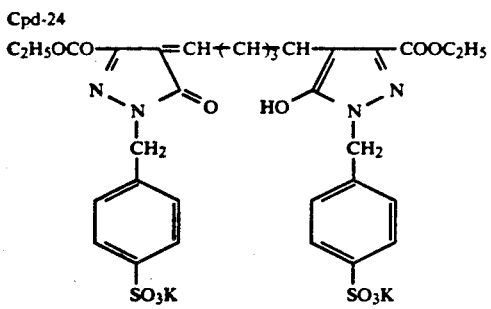
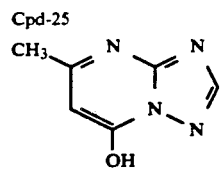
Cpd-26
Cpd-27
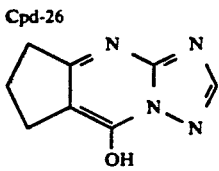
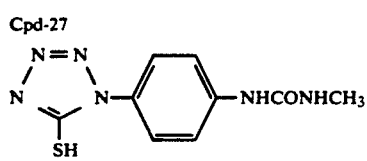
Cpd-28
ExC-1

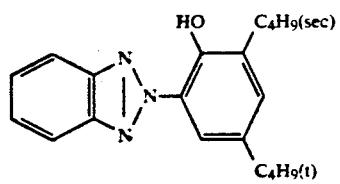

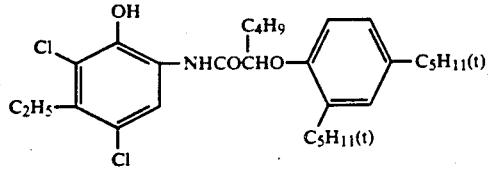

ExM-1

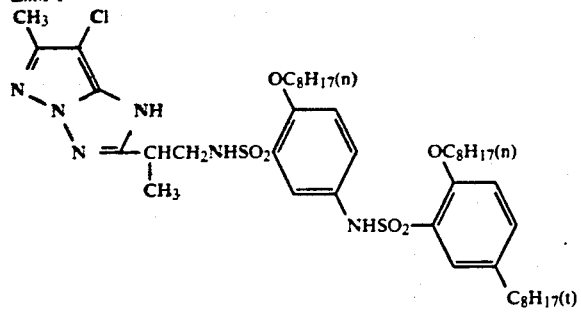

ExY-1

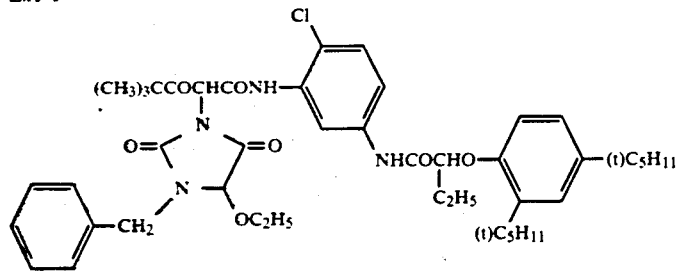

Solv-5
Di(2-ethylhexyl) Phthalate

Solv-7
Di(3-methylhexyl) Phthalate

Solv-9
Dibutyl Phthalate

Solv-6
Trinonyl Phosphate

Solv-8
Tricresyl Phosphate

Solv-10
Trioctyl Phosphate

The color reversal photographic material thus obtained was exposed to the same gradation of exposure as in the case of Example 5, and then subjected to the color reversal process (R-3 Process) as mentioned below.

| | R-3 Process | |
|---|---|---|
| Step | Temperature | Time |
| First Development (Black-and-white Development) | 38° C. | 1 min 15 sec |
| Rinsing with water | 38° C. | 1 min 30 sec |
| Reversal Exposure | 100 lux or more | 1 sec or more |
| Color Development | 38° C. | 2 min 15 sec |
| Rinsing with Water | 38° C. | 45 sec |
| Bleach-fixation | 38° C. | 2 min |
| Rinsing with Water | 38° C. | 2 min 15 sec |

The processing solution used in each step had the following composition.

| First Developer: | |
|---|---|
| Penta-sodium Nitrilo-N,N,N-trimethylene-phosphate | 0.6 g |
| Penta-sodium Diethylenetriamine-penta-acetate | 4.0 g |
| Potassium Sulfite | 30.0 g |
| Potassium Thiocyanate | 1.2 g |
| Potassium Carbonate | 35.0 g |

| -continued | |
|---|---|
| Potassium Hydroquinone-monosulfonate | 25.0 g |
| Diethylene Glycol | 15.0 ml |
| 1-Phenyl-4-hydroxymethyl-4-methyl-3-pyrazolidone | 2.0 g |
| Potassium Bromide | 0.5 g |
| Potassium Iodide | 5.0 mg |
| Water to make | 1 liter |
| (pH | 9.70) |
| Color Developer: | |
| Benzyl Alcohol | 15.0 ml |
| Diethylene Glycol | 12.0 ml |
| 3,6-Dithia-1,8-octanediol | 0.2 g |
| Penta-sodium Nitrilo-N,N,N-trimethylene-phosphate | 0.5 g |
| Penta-sodium Diethylenetriamine-penta-acetate | 2.0 g |
| Sodium Sulfite | 2.0 g |
| Potassium Carbonate | 25.0 g |
| Hydroxylamine Sulfate | 3.0 g |
| N-ethyl-N-($\beta$-methanesulfonamidoethyl)-3-methyl-4-aminoaniline Sulfate | 5.0 g |
| Potassium Bromide | 0.5 g |
| Potassium Iodide | 1.0 mg |
| Water to make | 1 liter |
| (pH | 10.40) |
| Bleach-fixing Solution: | |
| 2-Mercapto-1,3,4-triazole | 1.0 g |
| Disodium Ethylenediamine-tetraacetate Dihydrate | 5.0 g |
| Ammonium Ethylenediamine-tetraacetate/ | 80.0 g |

| -continued | |
|---|---|
| Fe(III) Monohydrate | |
| Sodium Sulfite | 15.0 g |
| Sodium Thiosulfate (700 g/liter solution) | 160.0 ml |
| Glacial Acetic Acid | 5.0 ml |
| Water to make | 1 liter |
| (pH | 6.50) |

The absorption spectrum of the color image thus obtained was measured in the same manner as in the previous Example 5. The results obtained showed that the color reversal photographic material of the present invention was also excellent like the photographic paper samples of the present invention in Example 5.

While the invention has been described in detail and with reference to specific embodiments thereof, it will be apparent to one skilled in the art that various changes and modifications can be made therein without departing from the spirit and scope thereof.

What is claimed is:

1. A pyrazoloazole cyan coupler of formula (IV), (V), or (VI):

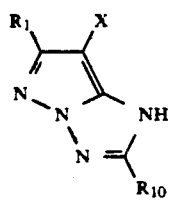 (IV)

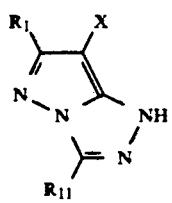 (V)

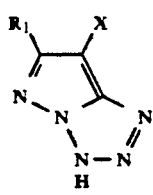 (VI)

wherein X represents a hydrogen atom, a halogen atom, a carboxyl group or a group bonded directly to a carbon atom of chemical structure as depicted in formulae (IV), (V), or (VI) via an oxygen atom, a nitrogen atom, a sulfur atom or a carbon atom, $R_1$ represents a substituent having a Hammett's substitutent constant of 0.6 to 2.0, and $R_{10}$ and $R_{11}$ each represents a hydrogen atom, a halogen atom, a straight chain or branched alkyl group, an aryl group, an alkoxy group, or an anilino group.

2. A pyrazoloazole coupler as in claim 1, wherein the coupler is a coupler represented by formula (IV)

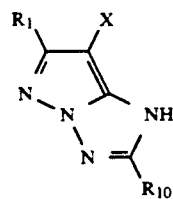 (IV)

wherein X $R_1$ and $R_{10}$ are defined as in claim 1.

3. A pyrazoloazole coupler as in claim 1, wherein $R_1$ represents a cyano group, a β-carboxyvinyl group, a nitro group, a trimethylammonium group, a trifluoromethanesulfonyl group, a trifluoromethanesulfinyl group, a difluoromethanesulfonyl group, a methanesulfonyl group, a dimethylphosphonium group, a benzenesulfonyl group or a β,β-dicyanovinyl group.

4. A pyrazoloazole coupler as in claim 1, wherein X represents a group bonded directly to the formula (I) structure via an oxygen or nitrogen atom.

5. A pyrazoloazole cyan coupler as claimed in claim 1, wherein $R_{10}$ and $R_{11}$ each represent an alkyl group or an aryl group.

6. A pyrazoloazole cyan coupler as claimed in claim 1, wherein $R_{10}$ is

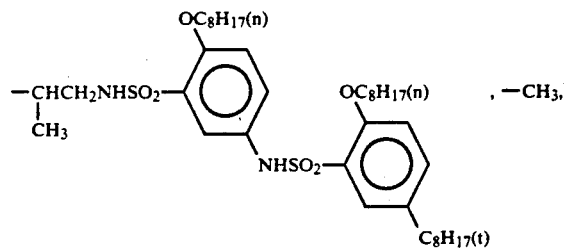

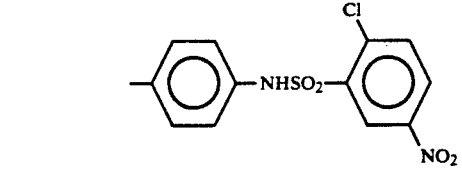

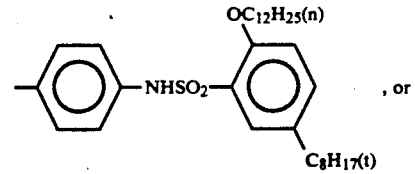

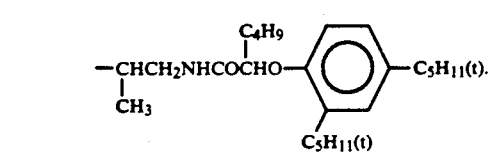

7. A pyrazoloazole cyan coupler as claimed in claim 1, wherein said coupler is

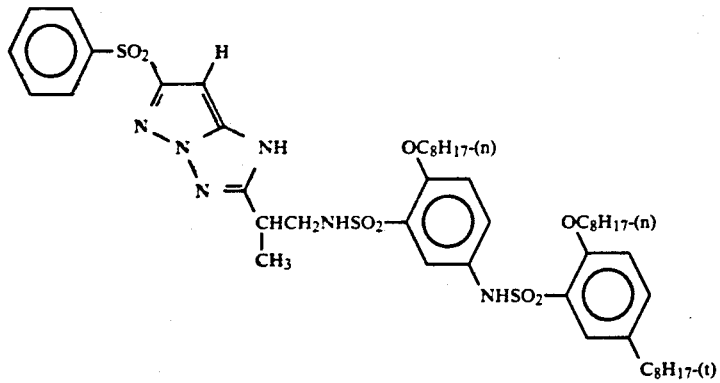
Compound No. 1
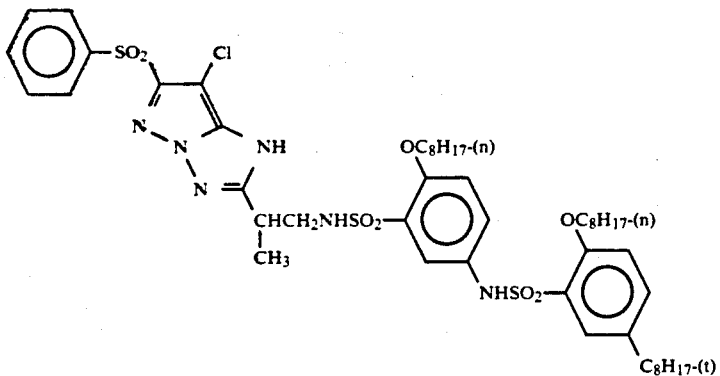
Compound No. 2
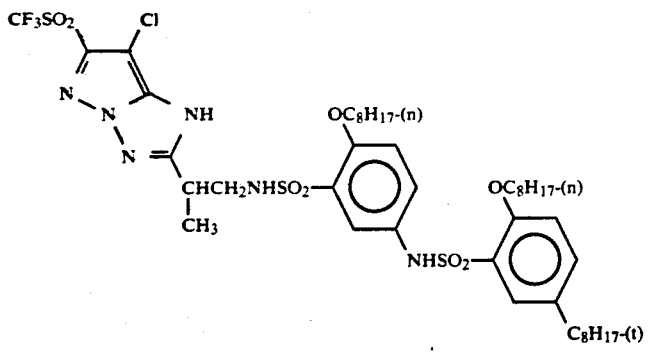
Compound No. 3
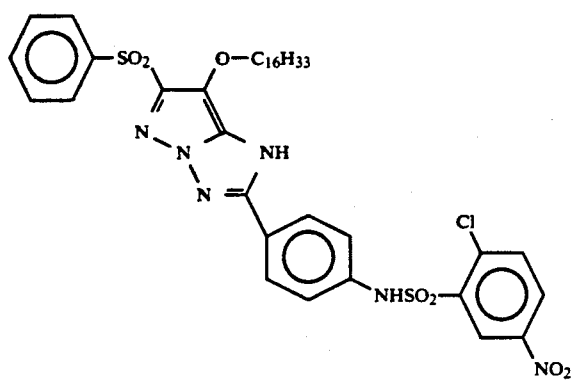
Compound No. 6

-continued
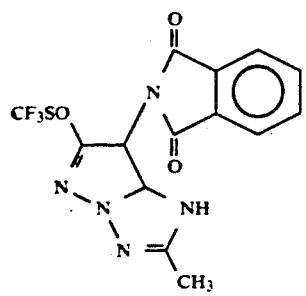
Compound No. 8
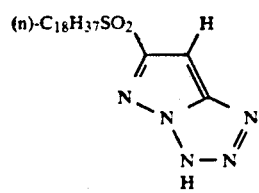
Compound No. 20
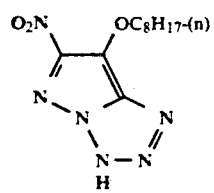
Compound No. 21
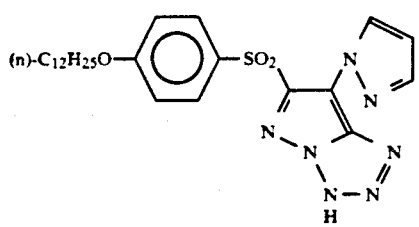
Compound No. 22
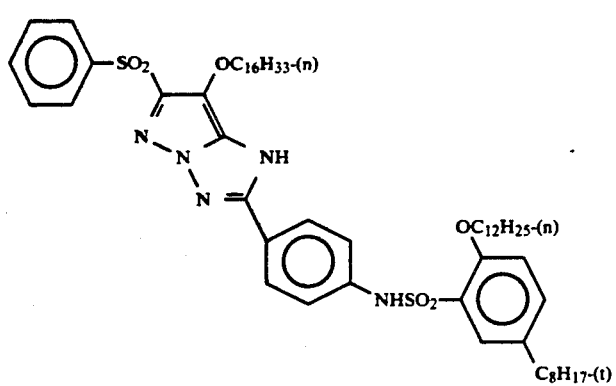
Compound No. 30

Compound No. 31

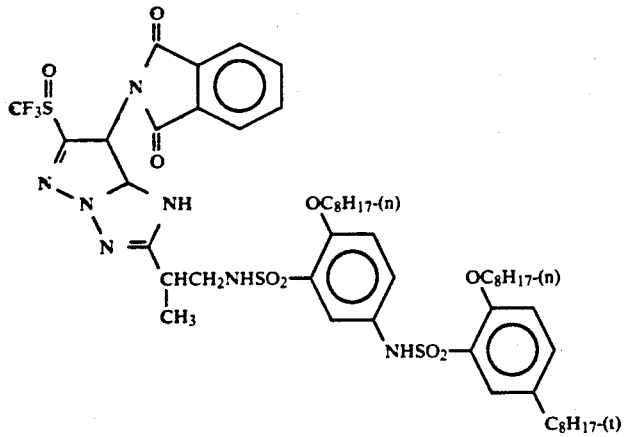

or

Compound No. 33

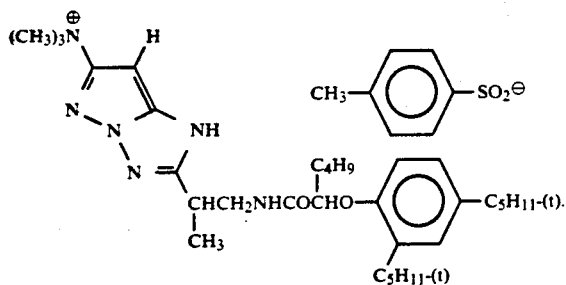

8. A pyrazoloazole cyan coupler as claimed in claim 1, wherein $R_1$ represents a cyano group, a β-carboxyvinyl group, a nitro group, a trimethylammonium group, a trifluoromethanesulfonyl group, a trifluoromethanesulfinyl group, a difluoromethanesulfonyl group, a methanesulfonyl group, a dimethylphosphonium group, a benzenesulfonyl group, or a β,β-dicyanovinyl group, a phenylsulfonium group and a methylsulfonium group.

* * * * *